(12) United States Patent
Van Wilt et al.

(10) Patent No.: US 12,361,263 B1
(45) Date of Patent: Jul. 15, 2025

(54) ARTIFICIAL INTELLIGENCE TECHNIQUES UTILIZING A GENERATIVE RELATIONAL NETWORK

(71) Applicant: The Joan and Irwin Jacobs Technion-Cornell Institute, New York, NY (US)

(72) Inventors: Yasmine Van Wilt, New York, NY (US); James Anderson, New York, NY (US); Brian E. Wallace, London (GB); Matthew Loftspring, Denver, CO (US)

(73) Assignee: The Joan and Irwin Jacobs Technion-Cornell Institute, New York, NY (US)

( * ) Notice: Subject to any disclaimer, the term of this patent is extended or adjusted under 35 U.S.C. 154(b) by 0 days.

(21) Appl. No.: 18/923,064

(22) Filed: Oct. 22, 2024

(51) Int. Cl.
*G06N 3/0475* (2023.01)
*G06N 3/082* (2023.01)
*G16H 20/30* (2018.01)

(52) U.S. Cl.
CPC .......... *G06N 3/0475* (2023.01); *G06N 3/082* (2013.01); *G16H 20/30* (2018.01)

(58) Field of Classification Search
CPC ....... G06N 3/0475; G06N 3/082; G16H 20/30
See application file for complete search history.

(56) References Cited

U.S. PATENT DOCUMENTS

| | | |
|---|---|---|
| 7,760,927 B2 | 7/2010 | Gholap et al. |
| 10,322,338 B2 | 6/2019 | Cozad et al. |
| 12,277,651 B1 | 4/2025 | Villongco et al. |
| 2011/0188713 A1 | 8/2011 | Chin et al. |
| 2020/0097841 A1 | 3/2020 | Petousis et al. |
| 2021/0000404 A1 | 1/2021 | Wang et al. |
| 2021/0270127 A1 | 9/2021 | Zhu et al. |

(Continued)

FOREIGN PATENT DOCUMENTS

| | | |
|---|---|---|
| KR | 20200133424 A | 11/2020 |
| WO | 2019191250 A1 | 10/2019 |
| WO | 2021043193 A1 | 3/2021 |

OTHER PUBLICATIONS

Palazzo, et al., "Generative Adversarial Networks Conditioned by Brain Signals", ICCV2017, 2017 (Year: 2017).*

(Continued)

*Primary Examiner* — Tsu-Chang Lee
(74) *Attorney, Agent, or Firm* — M&B IP Analysts, LLC

(57) ABSTRACT

A system and method for identifying relationships using relational networks. A method includes applying a generative relational network (GRN) in order to create a model of relationships between entities. The GRN includes multiple sets of nodes, where each set of nodes includes a respective set of machine learning models. The sets of nodes include dominance factor nodes and evolution of internal component nodes, where the dominance factor nodes define a dominance factor based on change intensity and change frequency, and the evolution of internal component nodes define evolution with respect to changes over time. Relationships among the entities are simulated using the model, and at least a portion of the relationships are eliminated for a target interaction based on the simulation results. The remaining relationships are tested with respect to the target interaction in order to identify the target interaction.

19 Claims, 9 Drawing Sheets

(56) References Cited

U.S. PATENT DOCUMENTS

| | | | |
|---|---|---|---|
| 2022/0164628 A1 | 5/2022 | Hahn | |
| 2023/0142885 A1 | 5/2023 | Laszlo et al. | |
| 2023/0260662 A1* | 8/2023 | Pao | G06N 3/088 |
| | | | 703/11 |
| 2023/0401430 A1 | 12/2023 | Zheng et al. | |
| 2024/0144141 A1 | 5/2024 | Cella et al. | |

OTHER PUBLICATIONS

Frassle, et al., "A generative model of whole-brain effective connectivity", NeuroImage 179 (2018) 505-529, 2018 (Year: 2018).*

Bryant, Erin. "Study Reveals How APOE4 Gene May Increase Risk for Dementia | National Institute on Aging." National Institute on Aging, Mar. 16, 2021, www.nia.nih.gov/news/study-reveals-how-apoe4-gene-may-increase-risk-dementia.

Cjhutto. "CJHUTTO/Vadersentiment: Vader Sentiment Analysis. Vader (Valence Aware Dictionary and Sentiment Reasoner) Is a Lexicon and Rule-Based Sentiment Analysis Tool That Is Specifically Attuned to Sentiments Expressed in Social Media, and Works Well on Texts from Other Domains." GitHub, github.com/cjhutto/vaderSentiment. Accessed Oct. 22, 2024.

Loria, Steven. "Simplified Text Processing¶." TextBlob, textblob.readthedocs.io/en/dev/. Accessed Oct. 22, 2024.

Andrew W. Senior, Richard Evans, John M. Jumper, James Kirkpatrick, L. Sifre, Tim Green, Chongli Qin, Augustin Zídek, Alexander W. R. Nelson, Alex Bridgland, Hugo Penedones, Stig Petersen, Karen Simonyan, Steve Crossan, Pushmeet Kohli, David T. Jones, David Silver, Koray Kavukcuoglu, and Demis Hassabis. 2020.Improved protein structure prediction using potentials from deep learning. Nature 577 (2020), 706-710.

Hang Li, Xiujun Gong, Hua Yu, and Chang Zhou. 2018. Deep Neural Network Based Predictions of Protein Interactions Using Primary Sequences. Molecules : A Journal of Synthetic Chemistry and Natural Product Chemistry 23 (2018).https://api.semanticscholar.org/CorpusID:51906277.

Hongwei Wang, Weijian Li, Xiaomeng Jin, Kyunghyun Cho, Heng Ji, Jiawei Han, and Martin D. Burke. 2021. Chemical-Reaction-Aware Molecule Representation Learning.ArXiv abs/2109.09888 (2021).https://api.semanticscholar.org/CorpusID:237581512.

Iain H. Moal and Juan Fernandez-Recio. 2012.SKEMPI: a Structural Kinetic and Energetic database of Mutant Protein Interactions and its use in empirical models. Bioinformatics 28 20 (2012), 2600-7.https://api.semanticscholar.org/CorpusID:39983995.

Mohammed AlQuraishi. 2019.ProteinNet: a standardized data set for machine learning of protein structure. BMC bioinformatics 20 (2019), 1-10. Ashburner et al. (2000).

Muhao Chen, Chelsea J.-T. Ju, Guangyu Zhou, X. Chen, Tianran Zhang, Kai-Wei Chang, Carlo Zaniolo, and Wei Wang. 2019. Multifaceted protein-protein interaction prediction based on Siamese residual RCNN. Bioinformatics 35 (2019), i305-i314.https://api.semanticscholar.org/CorpusID:196809757.

Zhengyan Zhang, Xu Han, Zhiyuan Liu, Xin Jiang, Maosong Sun, and Qun Liu. 2019. ERNIE: Enhanced Language Representation with Informative Entities. In Annual Meeting of the Association for Computational Linguistics.

"Improving mode exploring capability of generative adversarial nets by self-organizing map." Neurocomputing 576 (2024): 127244; Retrieved from the Internet: Li, Wei, Yongxing He, and Yongchuan Tang Apr. 1, 2024 (Apr. 1, 2024) The whole document.

Ancient Neuromodulation by Vasopressin/Oxytocin-Related Peptides. Andrea Agiollo and Andrea Omicini. 2022.GNN2GNN: Graph neural networks to generate neural networks. In Conference on Uncertainty in Artificial Intelligence.https://api.semanticscholar.org/CorpusID:252898899, AlQuraishi (2019).

Ba X. et al. Three-day continuous oxytocin infusion attenuates thermal and mechanical nociception by rescuing neuronal chloride homeostasis via upregulation KCC2 expression and function. Front Pharmacol. 13, 845018 (2022).

Breton J.-D. et al. Oxytocin-induced antinociception in the spinal cord is mediated by a subpopulation of glutamatergic neurons in lamina I-II which amplify GABAergic inhibition. Mol. Pain 4, https://doi.org/10.1186/1744-8069-4-19 (2004).

Franco Scarselli, Marco Gori, Ah Chung Tsoi, Markus Hagenbuchner, and Gabriele Monfardini. 2009.The Graph Neural Network Model. IEEE Transactions on Neural Networks 20 (2009), 61-80.https://api.semanticscholar.org/CorpusID:206756462.

Hathway, G. et al. A postnatal switch in GABAergic control of spinal cutaneous reflexes. Eur. J. Neurosci. 23, 112-118 (2006).

Heyn J, Azad SC, Luchting B. Altered regulation of the T-cell system in patients with CRPS. Inflamm Res. 2018;68(1): Abstract. https://link.springer.com/article/10.1007/s00011-018-1182-3. https://doi.org/10.1007/s00011-018-1182-3.

Higashida, H., Oshima, Y. & Yamamoto, Y. Oxytocin transported from the blood across the blood-brain barrier by receptor for advanced glycation end-products (RAGE) affects brain function related to social behavior. Peptides 178, 171230 (2024).

International Search Report for PCT/IB2024/060379, dated Jan. 30, 2025. Searching Authority, Israel Patent Office, Jerusalem, Israel.

International Search Report for PCT/IB2024/060380, dated Jan. 30, 2025. Searching Authority, Israel Patent Office, Jerusalem, Israel.

Jiajia Liu, Mengyuan Yang, Yankai Yu, Haixia Xu, Kang Li, and Xiaobo Zhou. 2024. Large language models in bioinformatics: applications and perspectives.ArXiv (2024). https://api.semanticscholar.org/CorpusID:266899789.

Jie Hou, Badri Adhikari, and Jianlin Cheng. 2017.DeepSF: deep convolutional neural network for mapping protein sequences to folds.Bioinformatics 34 (2017), 1295-1303.https://api.semanticscholar.org/CorpusID:4891436.

Juif, P. E. & Poisbeau, P. Neurohormonal effects of oxytocin and vasopressin receptor agonists on spinal pain processing in male rats. Pain 154, 1449-1456 (2013).

Kim K, DeSalles A, Johnson J, Ahn S. Sympathectomy: open and thorascopic. In: Burchiel K, editor. Surgical Management of Pain. New York: Thieme Publishers; 2002. p. 688-690.

Leonzino, M. et al. The timing of the excitatory-to-inhibitory GABA switch is regulated by the oxytocin receptor via KCC2. Cell Rep. 15, 96-103 (2016).

Liang Yao, Chengsheng Mao, and Yuan Luo. 2019.KG-BERT: Bert for Knowledge Graph Completion. CoRR abs/1909.03193 (2019). https://api.semanticscholar.org/CorpusID:202539519.

M. Schlichtkrull, Thomas Kipf, Peter Bloem, Rianne van den Berg, Ivan Titov, and Max Welling. 2017.Modeling Relational Data with Graph Convolutional Networks. In Extended Semantic Web Conference. https://api.semanticscholar.org/CorpusID:5458500.

Mens, W. B. J., Wtter, A., Van, T. B. & Greidanus, W. Penetration of Neurohypophyseal Hormones from Plasma into Cerebrospinal Fluid (CSF) Half-Times of Disappearance of These Neuropeptides from CSF. Brain Res. 262, 143-149 (1983).

Millan, M. J. Descending control of pain. Prog. Neurobiol. 66, 355-474 (2002).

Misidou C, Papagoras C. Complex regional pain syndrome: an update. Mediterr J Rheumatol. 2019;30(1):16-25. https://www.ncbi.nlm.nih.gov/pubmed/32185338. https://doi.org/10.31138/mjr.30.1.16.

Nadav Brandes, Dan Ofer, Yam Peleg, Nadav Rappoport, and Michal Linial. 2021.ProteinBERT: a universal deep-learning model of protein sequence and function.Bioinformatics 38 (2021), 2102-2110.

Ningyu Zhang, Zhen Bi, Xiaozhuan Liang, Siyuan Cheng, Haosen Hong, Shumin Deng, Qiang Zhang, Jiazhang Lian, and Huajun Chen. 2022.OntoProtein: Protein Pretraining With Gene Ontology Embedding. In International Conference on Learning Representations. https://openreview.net/forum?id=yfe1VMYAXa4.

Poisbeau P., Grinevich V., Charlet A. Oxytocin signaling in pain: cellular, circuit, system, and behavioral levels. Behavioral pharmacology of neuropeptides: oxytocin. 193-211. (2018).

Ruoxi Sun. 2022.Does GNN Pretraining Help Molecular Representation? https://export.arxiv.org/pdf/2207.06010v2.pdfArXiv abs/2207.06010 (2022). https://api.semanticscholar.org/CorpusID:250493139.

(56) References Cited

OTHER PUBLICATIONS

Somaye Hashemifar, Behnam Neyshabur, Aly A Khan, and Jinbo Xu. 2018.Predicting protein-protein interactions through sequence-based deep learning.Bioinformatics 34, 17 (Sep. 2018), i802-i810. https://doi.org/10.1093/bioinformatics/bty573 arXiv:https://academic.oup.com/bioinformatics/article-pdf/34/17/1802/50582268/bioinformatics_34_17_i802.pdf.

Thomas N. Kipf and Max Welling. 2017.Semi-Supervised Classification with Graph Convolutional Networks. In International Conference on Learning Representations.https://openreview.net/forum?id=SJU4ayYgl.

Welli Nie, Relgan: Relational Generative Adversarial Networks for Text Generation, 2019 (Year:2019).

Written Opinion of the Searching Authority for PCT/IB2024/060379, dated Jan. 30, 2025. Searching Authority, Israel Patent Office, Jerusalem, Israel.

Written Opinion of the Searching Authority for PCT/IB2024/060380, dated Jan. 30, 2025. Searching Authority, Israel Patent Office, Jerusalem, Israel.

Xuewei Li, A structure-enhanced generative adversarial network for knowledge graph zero-shot relational learning, 2023 (Year: 2023).

Yijia Xiao, Jiezhong Qiu, Ziang Li, Chang-Yu Hsieh, and Jie Tang. 2021. Modeling Protein Using Large-scale Pretrain Language Model. ArXiv abs/2108.07435 (2021).

* cited by examiner

ARTIFICIAL INTELLIGENCE TECHNIQUES UTILIZING A GENERATIVE RELATIONAL NETWORK

TECHNICAL FIELD

The present disclosure relates generally to artificial intelligence, and more specifically to using machine learning architectures designed to learn evolution of internal components.

BACKGROUND

Artificial intelligence systems, and in particular systems using machine learning, have been proven effective at learning patterns in data. These patterns may be utilized for purposes such as, but not limited to, identifying causal relationships. However, existing machine learning solutions face challenges in modeling complex mechanisms with many interacting components. Techniques for allowing machine learning models to be utilized to effectively model such complex mechanisms would therefore be desirable.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments, and is intended to neither identify key or critical elements of all embodiments nor to delineate the scope of any or all aspects. Its sole purpose is to present some concepts of one or more embodiments in a simplified form as a prelude to the more detailed description that is presented later. For convenience, the term "some embodiments" or "certain embodiments" may be used herein to refer to a single embodiment or multiple embodiments of the disclosure.

Certain embodiments disclosed herein include a method for identifying relationships using relational networks. The method comprises: applying a generative relational network (GRN) in order to create a model of relationships between entities among a plurality of entities, wherein the GRN includes a plurality of sets of nodes, each set of nodes including a respective set of machine learning models, wherein the plurality of sets of nodes include a set of dominance factor nodes and a set of evolution of internal component nodes, wherein the set of dominance factor nodes defines a dominance factor based on change intensity and change frequency, wherein the set of evolution of internal component nodes defines evolution with respect to changes determined based on values of the dominance factor over time; simulating a plurality of relationships among the plurality of entities using the model in order to produce simulation results; eliminating at least a portion of the plurality of relationships for a target interaction based on the simulation results in order to determine a set of remaining relationships for the target interaction; testing relationships among the set of remaining relationships with respect to the target interaction; and identifying the target interaction based on the testing of the relationships among the set of remaining relationships.

Certain embodiments disclosed herein also include a non-transitory computer readable medium having stored thereon causing a processing circuitry to execute a process, the process comprising: applying a generative relational network (GRN) in order to create a model of relationships between entities among a plurality of entities, wherein the GRN includes a plurality of sets of nodes, each set of nodes including a respective set of machine learning models, wherein the plurality of sets of nodes include a set of dominance factor nodes and a set of evolution of internal component nodes, wherein the set of dominance factor nodes defines a dominance factor based on change intensity and change frequency, wherein the set of evolution of internal component nodes defines evolution with respect to changes determined based on values of the dominance factor over time; simulating a plurality of relationships among the plurality of entities using the model in order to produce simulation results; eliminating at least a portion of the plurality of relationships for a target interaction based on the simulation results in order to determine a set of remaining relationships for the target interaction; testing relationships among the set of remaining relationships with respect to the target interaction; and identifying the target interaction based on the testing of the relationships among the set of remaining relationships.

Certain embodiments disclosed herein also include a system for identifying relationships using relational networks. The system comprises: a processing circuitry; and a memory, the memory containing instructions that, when executed by the processing circuitry, configure the system to: apply a generative relational network (GRN) in order to create a model of relationships between entities among a plurality of entities, wherein the GRN includes a plurality of sets of nodes, each set of nodes including a respective set of machine learning models, wherein the plurality of sets of nodes include a set of dominance factor nodes and a set of evolution of internal component nodes, wherein the set of dominance factor nodes defines a dominance factor based on change intensity and change frequency, wherein the set of evolution of internal component nodes defines evolution with respect to changes determined based on values of the dominance factor over time; simulate a plurality of relationships among the plurality of entities using the model in order to produce simulation results; eliminate at least a portion of the plurality of relationships for a target interaction based on the simulation results in order to determine a set of remaining relationships for the target interaction; test relationships among the set of remaining relationships with respect to the target interaction; and identify the target interaction based on the testing of the relationships among the set of remaining relationships.

Certain embodiments disclosed herein include the method, non-transitory computer readable medium, or system noted above or below, wherein the GRN is trained based on a visualization created using a self-organizing map.

Certain embodiments disclosed herein include the method, non-transitory computer readable medium, or system noted above or below, further including or being configured to perform the following step or steps: simulating a plurality of activities.

Certain embodiments disclosed herein include the method, non-transitory computer readable medium, or system noted above or below, further including or being configured to perform the following step or steps: analyzing the simulation results in order to determine whether an expected reaction is demonstrated in the simulation results for each of the simulated plurality of relationships and eliminating each relationship for which the simulation results lack the expected reaction.

Certain embodiments disclosed herein include the method, non-transitory computer readable medium, or system noted above or below, further including or being configured to perform the following step or steps: identifying a first entity among the plurality of entities, wherein the first entity is involved in the target interaction.

Certain embodiments disclosed herein include the method, non-transitory computer readable medium, or system noted above or below, wherein the plurality of entities is a plurality of neurotransmitters, wherein the plurality of relationships correspond to a plurality of respective locations, further including or being configured to perform the following step or steps: identifying a first neurotransmitter of the plurality of neurotransmitters, wherein the first neurotransmitter is identified as being a neurotransmitter of the target interaction based on the locations of the relationships among the set of remaining relationships.

Certain embodiments disclosed herein include the method, non-transitory computer readable medium, or system noted above or below, further including or being configured to perform the following step or steps: treating a patient by stimulating the patient with respect to the first neurotransmitter.

Certain embodiments disclosed herein include the method, non-transitory computer readable medium, or system noted above or below, wherein the first neurotransmitter is identified with respect to one of the locations of the relationships among the set of remaining relationships, wherein the patient is stimulated at least at the location of the target neurotransmitter.

Certain embodiments disclosed herein include the method, non-transitory computer readable medium, or system noted above or below, further including or being configured to perform the following step or steps: delivering a repetitive transcranial magnetic stimulation.

Certain embodiments disclosed herein include the method, non-transitory computer readable medium, or system noted above or below, further including or being configured to perform the following step or steps: providing at least one media stimulus to the patient.

Certain embodiments disclosed herein include the method, non-transitory computer readable medium, or system noted above or below, further including or being configured to perform the following step or steps: adjusting at least one stimulation parameter based on inputs captured while the patient is being stimulated, wherein the at least one stimulation parameter is adjusted based on a target outcome defined with respect to the inputs captured while the patient is being stimulated.

Certain embodiments disclosed herein include a method for training relational networks. The method comprises: applying a self-organizing map (SOM) to training data in order to create a visualization of the training data, wherein the SOM is a neural network configured to transform relationships between data items among a plurality of data items, wherein the visualization has a lower dimensionality than the training data; and training a plurality of machine learning models of a generative relational network (GRN) based on the visualization, wherein the GRN includes a plurality of sets of nodes having respective machine learning models among the plurality of machine learning models of the GRN, wherein the plurality of sets of nodes include a set of dominance factor nodes and a set of evolution of internal component nodes, wherein the set of dominance factor nodes defines a dominance factor based on change intensity and change frequency, wherein the set of evolution of internal component nodes defines evolution with respect to changes determined based on values of the dominance factor over time.

Certain embodiments disclosed herein also include a non-transitory computer readable medium having stored thereon causing a processing circuitry to execute a process, the process comprising: applying a self-organizing map (SOM) to training data in order to create a visualization of the training data, wherein the SOM is a neural network configured to transform relationships between data items among a plurality of data items, wherein the visualization has a lower dimensionality than the training data; and training a plurality of machine learning models of a generative relational network (GRN) based on the visualization, wherein the GRN includes a plurality of sets of nodes having respective machine learning models among the plurality of machine learning models of the GRN, wherein the plurality of sets of nodes include a set of dominance factor nodes and a set of evolution of internal component nodes, wherein the set of dominance factor nodes defines a dominance factor based on change intensity and change frequency, wherein the set of evolution of internal component nodes defines evolution with respect to changes determined based on values of the dominance factor over time.

Certain embodiments disclosed herein also include a system for training relational networks. The system comprises: a processing circuitry; and a memory, the memory containing instructions that, when executed by the processing circuitry, configure the system to: apply a self-organizing map (SOM) to training data in order to create a visualization of the training data, wherein the SOM is a neural network configured to transform relationships between data items among a plurality of data items, wherein the visualization has a lower dimensionality than the training data; and train a plurality of machine learning models of a generative relational network (GRN) based on the visualization, wherein the GRN includes a plurality of sets of nodes having respective machine learning models among the plurality of machine learning models of the GRN, wherein the plurality of sets of nodes include a set of dominance factor nodes and a set of evolution of internal component nodes, wherein the set of dominance factor nodes defines a dominance factor based on change intensity and change frequency, wherein the set of evolution of internal component nodes defines evolution with respect to changes determined based on values of the dominance factor over time.

Certain embodiments disclosed herein include the method, non-transitory computer readable medium, or system noted above or below, further including or being configured to perform the following step or steps: interpolating a plurality of data points using the trained plurality of machine learning models of the GRN; and retraining the plurality of machine learning models of the GRN using the interpolated plurality of data points Certain embodiments disclosed herein include the method, non-transitory computer readable medium, or system noted above or below, wherein the training data is a first set of training data, further including or being configured to perform the following step or steps: comparing the interpolated plurality of data points to a second set of training data in order to determine an error; and adjusting at least one parameter of the plurality of machine learning models of the GRN based on the determined error.

Certain embodiments disclosed herein include the method, non-transitory computer readable medium, or system noted above or below, wherein the interpolated plurality of data points is a first plurality of interpolated data points, further including or being configured to perform the following step or steps: interpolating a second plurality of interpolated data points using the retrained plurality of machine learning models of the GRN; and retraining the plurality of machine learning models of the GRN using the second plurality of interpolated data points.

Certain embodiments disclosed herein include the method, non-transitory computer readable medium, or system noted above or below, wherein the training data is a first set of training data, further including or being configured to perform the following step or steps: replacing at least a portion of the interpolated plurality of data points with data points of a second set of training data.

Certain embodiments disclosed herein include the method, non-transitory computer readable medium, or system noted above or below, further including or being configured to perform the following step or steps: adjusting at least one parameter of the plurality of machine learning models of the GRN based on the interpolated plurality of data points.

Certain embodiments disclosed herein include the method, non-transitory computer readable medium, or system noted above or below, wherein the changes are a second set of changes, wherein the plurality of sets of nodes further include a set of compounding change nodes, wherein the set of compounding change nodes defines compounding anomalies with respect to dominance and differences from a first set of changes over time.

Certain embodiments disclosed herein include the method, non-transitory computer readable medium, or system noted above or below, wherein the SOM includes a plurality of nodes representing respective entities of a plurality of entities, the plurality of nodes having a plurality of weights collectively defining the visualization, wherein each node has a respective weight of the plurality of weights representing a position of the node in an input space.

Certain embodiments disclosed herein include the method, non-transitory computer readable medium, or system noted above or below, further including or being configured to perform the following step or steps: establishing a plurality of edges between nodes among the plurality of nodes of the SOM based on proximity between the nodes among the plurality of nodes of the SOM, wherein the edges of the plurality of edges represent relationships between entities among the entities represented by respective nodes of the plurality of nodes.

BRIEF DESCRIPTION OF THE DRAWINGS

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

DETAILED DESCRIPTION

Figure 1:
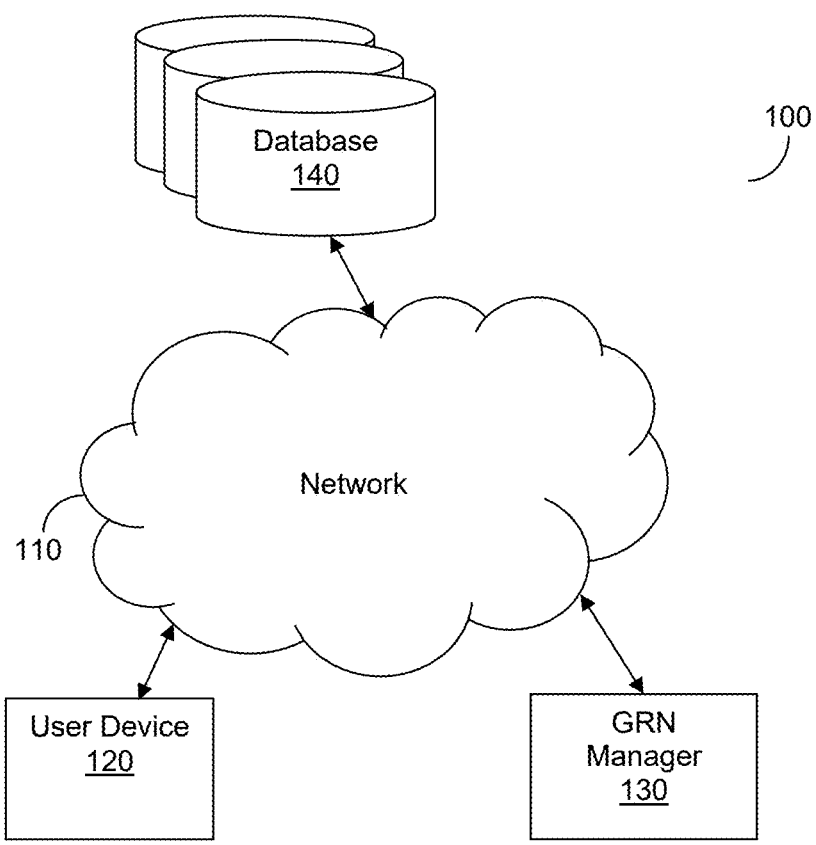
FIG. 1 is a network diagram utilized to describe various disclosed embodiments.

The various disclosed embodiments include techniques and systems utilizing a generative relational network (GRN) leveraging a dynamic and adaptive ontology in order to provide a machine learning (ML) architecture, which in turn may be utilized to realize artificial intelligence (AI) solutions which analyze confounding factors, potential correlations, and potential causal relationships between discrete ontological entities. Various disclosed embodiments may be utilized as a tool for continuously gathering, parsing, grouping, and revising data continuously as new data is added, thereby allowing for improving efficiency and speed of AI-based analysis. In particular, various disclosed embodiments may be applied in order to analyze discrete symptoms extracted from different sources of data in order to identify ontological relationships between neurobiological disease states which have related symptoms or otherwise to analyze internal mechanisms in order to identify ontological relationships between components of complex systems.

In accordance with various disclosed embodiments, a dynamic ontology is continuously updated based on incoming data and relationships based on both local and global contexts. Accordingly, the ontology may dynamically evolve over time as new data is obtained. Moreover, the GRN architectures discussed herein utilize expansive and modular architectures, which provides a flexible approach to learning ontological relationships using machine learning.

Additionally, a GRN as described herein may demonstrate various improvements over existing solutions. In particular, certain existing ML models such as generative adversarial networks (GANs) and graph neural networks (GNNs) may provide techniques for learning certain relationships. However, these and other types of ML models do not inherently factor in the temporal dimension of frequency of data changes, and particularly do not utilize such factors as dominant factors for evolving the models over time. The GRN in accordance with various disclosed embodiments may utilize temporal factors such as time and frequency as dominant factors, which provides a new approach to anomaly detection and ontology.

In certain embodiments, values of a dominance factor may be related to intensities and frequencies of changes over time. To this end, in such embodiments, the dominance factor at a given time may be defined based on an intensity of change and a frequency of change as of that time. This relationship between dominance factor values with intensities and frequencies may be modeled and learned via machine learning. Moreover, in accordance with various disclosed embodiments, anomalies may be compounded over time based on the values of the dominant factor in order to determine anomaly compounding values. These anomaly compounding values, in turn, can be utilized to determine values representing the evolution or understanding of an internal component, and such an evolution of the internal component may be modeled and learned via machine learning. In this regard, in at least some embodiments, both the relationship between dominance factor and frequencies and intensities of changes, as well as the relationship between an evolution of an internal component and anomaly compounding values based on values of the dominance factor, may be learned using machine learning by training respective machine learning models.

In this regard, it is noted that, as anomalies compound over time, those anomalies may affect the evolution or understanding of an internal component. A dominance factor which reflects both intensity and frequency of changes may be leveraged in order to effectively represent these evolutions over time. Accordingly, various disclosed embodiments utilize ML architectures and techniques which account for intensity and frequency of changes as part of dominant factors in order to allow for learning relationships between components over time.

It is also noted that interpolants, or estimated values that bridge gaps in datasets, may provide additional context when dealing with missing or sparse data, thereby enabling more continuous and comprehensive data analysis. Such continuity may be relevant for certain use cases such as, but not limited to, time-series forecasting and regression analysis. Further, a technical challenge with machine learning models is training models which become overfitted, which may be more likely to occur when training using sparse datasets such that the model "learns" the noise rather than the underlying pattern. Additionally, utilizing interpolants as described herein may allow for accurately analyzing trends, patterns, and behaviors which would otherwise not be possible to analyze due to missing data.

Given the above, it has been identified that self-organizing maps (SOMs) may be leveraged in order to facilitate machine learning for evolution of internal components. Such SOMs are realized via a neural network used for data visualization and dimensionality reduction. SOMs may be utilized to transform complex, nonlinear relationships between high-dimensional data items into simpler geometric relationships on a low-dimensional display.

Various aspects of the disclosed embodiments may allow for analyzing data, and in particular for analyzing data related to genetic traits of organisms such as, but not limited to, phenotypic data and genotypic data. In particular, the improved analysis of confounding factors, potential correlations, and potential causal relationships provided via various disclosed embodiments may allow for identifying latent relationships between phenotypes and genotypes, or between phenotypes or genotypes with other traits or characteristics of organisms. More specifically, various disclosed embodiments may be leveraged to discern and integrated explicitly annotated data (e.g., phenotypic data) and related but unannotated or otherwise implicit data (e.g., genotypic data), thereby allowing for using machine learning to represent a more holistic understanding of such relationships.

In particular, clusters of nodes in a SOM may be utilized to represent groupings of similar data points or otherwise to represent entities having similar properties, and phenotypic and genotypic relationships can be visualized on the SOM, thereby allowing for highlighting clusters and potential relationships between different types of data.

Various disclosed embodiments may be utilized for different use cases including, but not limited to, biological analysis (e.g., analyzing functions of biological components in the body), chemical analysis (e.g., discovering drugs or other chemical components which might be used in chemical compositions for different purposes), and more. That is, although various embodiments are discussed with respect to the central nervous system (CNS) and using GRNs to identify interactions which may be indicative of the existences of certain hypothesized neurotransmitters, various disclosed embodiments may be equally applicable to other kinds of internal mechanisms that play hidden roles in certain functions of systems capable of being modeled via the SOM and GRN as discussed herein. In the natural sciences, such systems may include systems such as, but not limited to, life science (i.e., biology) systems or physical science (e.g., physics, chemistry, earth science, astronomy, electricity, materials, etc.) systems. As a non-limiting example, certain disclosed embodiments may be applicable to other types of diagnosis or other clinical applications.

To this end, it is noted that the ontologies described herein may be defined in a robust manner in order to allow the architecture described herein to be applied more readily to different use cases. Moreover, ontologies may be defined specifically for certain use cases depending on an expected level of granularity of the internal mechanisms to be modeled through these ontologies which may be unearthed using various processes and machine learning architectures described herein. This may allow for effectively fine tuning the ontologies for different use cases, which in turn may further improve the accuracy, efficiency, or both, of subsequent processing (e.g., processing via a SOM, GRN, or both). As a non-limiting example, for implementations involving the central nervous system, the ontologies may be defined using neurotransmitter or other nerve-specific concepts in order to tune the process toward unearthing hidden mechanisms behind certain biological functions related to neurotransmitters; for implementations involving the digestive system or other anatomical systems (e.g., respiratory system, circulatory system, endocrine system, exocrine system, immune system, muscular and/or skeletal systems, etc.), ontologies may be defined using organ-specific concepts or other concepts relating to components of such anatomical systems in order to model internal mechanisms of those systems which may not have been directly observed or measured.

The level of granularity to be modeled in order to effectively tailor the GRN architecture to different use cases may depend on the level of granularity of the internal mechanism to be modeled. As a non-limiting example, different levels of granularity for various biological process modeling may include modeling at the chemical level, at the macromolecule or subcellular level, at the cellular level, at the tissue level (i.e., a level made up of groups of cells), at the organ level (i.e., a level made of tissues working together), at the organ system level (i.e., a level made of organs working together to perform a function), at the organism level, at a population level, at an environment level, and the like.

Moreover, various disclosed embodiments are discussed with respect to natural science applications, but the disclosed embodiments are not necessarily limited as such. Various disclosed embodiments may be utilized to model and analyze artificial systems such as, but not limited to, computer systems or other aspects of computer science. As a non-limiting example, certain disclosed embodiments may be utilized to model internal mechanisms used for machine learning such as, but not limited to, the hidden layers in a neural network, in order to identify certain nodes or other components which may play a certain role within the hidden layer and may therefore have a particular impact on the machine learning process.

FIG. 1 shows an example network diagram 100 utilized to describe the various disclosed embodiments. In the example network diagram 100, a user device 120, a generative relational network (GRN) manager 130, and one or more databases 140-1 through 140-N (hereinafter referred to individually as a database 140 and collectively as databases 140, merely for simplicity purposes) communicate via a network 110. The network 110 may be, but is not limited to, a wireless, cellular or wired network, a local area network (LAN), a wide area network (WAN), a metro area network (MAN), the Internet, the worldwide web (WWW), similar networks, and any combination thereof.

The user device (UD) 120 may be, but is not limited to, a personal computer, a laptop, a tablet computer, a smartphone, a wearable computing device, or any other device capable of receiving and displaying notifications.

The GRN manager 130 is configured to utilize one or more machine learning models as part of a GRN architecture as described herein. As discussed herein, such a GRN architecture may be designed to learn how internal components evolve by accounting for the temporal dimension of frequency of data changes with respect to the influence of a dominance factor. More specifically, the GRN architecture may account for anomaly compounding over time in order to achieve a machine learning architecture which effectively understands the impacts of such compounding anomalies over time. To this end, the GRN architecture accounts for intensity and frequency of changes as part of dominant factors in order to learn relationships between components over time.

To aid in various disclosed embodiments, the GRN manager 130 may be configured to further utilize a self-organizing map (SOM) in order to facilitate learning the evolution of internal components. Such a SOM may be realized via a neural network, and may be utilized to represent clusters of similar data points, thereby allowing for highlighting clusters and potential relationships between different types of data.

The databases 140 may be or may include databases storing data to be used for training machine learning models, to be analyzed via the GRN architecture as described herein, or both. In some embodiments where the GRN architecture is utilized in order to analyze genetic traits of organisms, the data may be or may include phenotypic data, genotypic data, both, and the like, or data otherwise related to phenotypes and genotypes of organisms.

It should be noted that FIG. 1 depicts an implementation of various disclosed embodiments, but that at least some disclosed embodiments are not necessarily limited as such. Other deployments, arrangements, combinations, and the like, may be equally utilized without departing from the scope of the disclosure.

Figure 2:
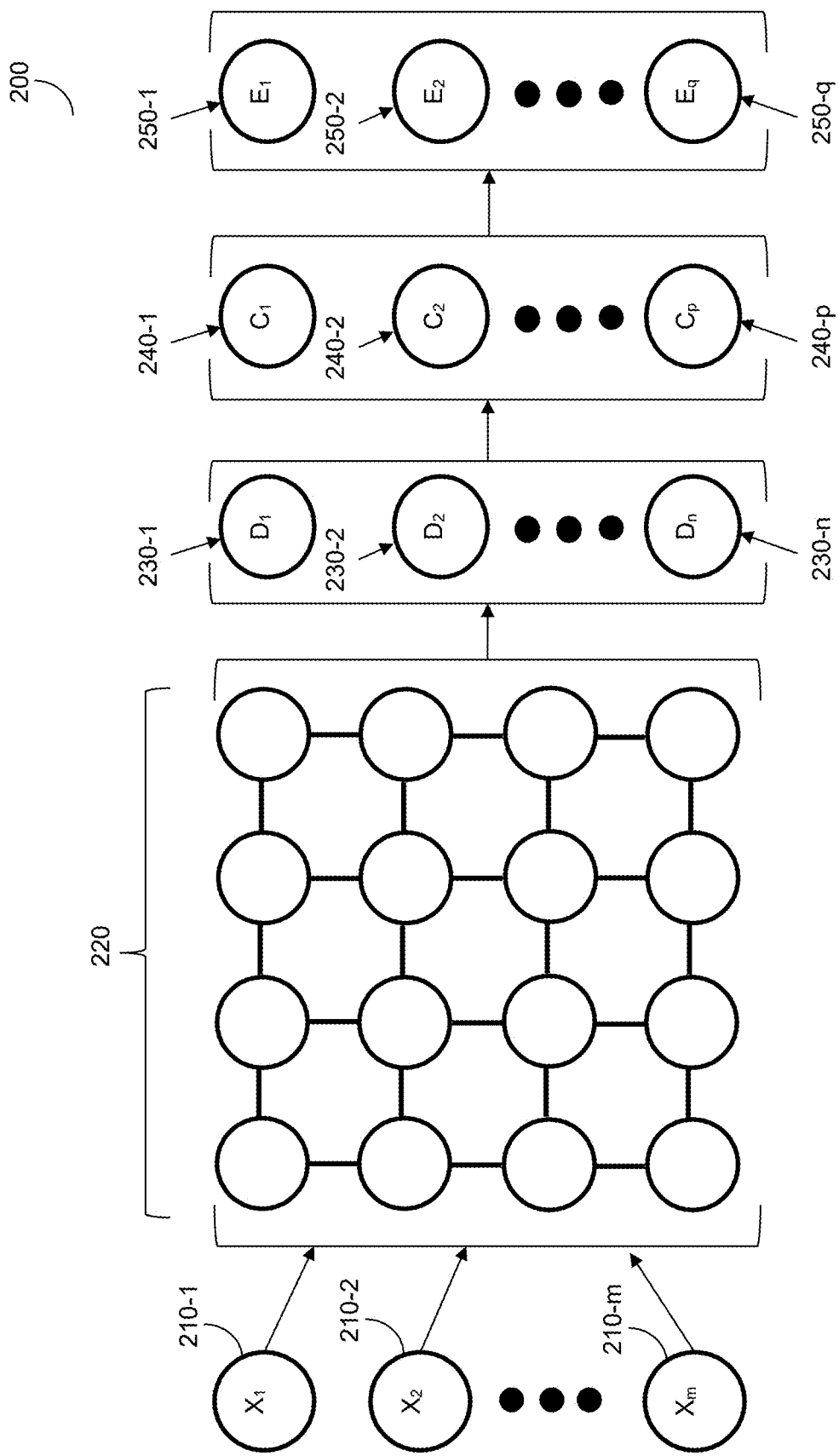
FIG. 2 is an architectural diagram illustrating a machine learning architecture including a generative relational network according to an embodiment.

FIG. 2 is an architectural diagram 200 illustrating a machine learning architecture including a generative relational network (GRN) according to an embodiment. As depicted in FIG. 2, the GRN architecture includes a set of input nodes 210-1 through 210-$m$ (referred to as input nodes 210 for simplicity), a self-organizing map (SOM) 220, a set of dominance factor nodes 230-1 through 230-$n$ (referred to as dominance factor nodes 230 for simplicity), a set of compounding change nodes 240-1 through 240-$p$ (referred to as compounding change nodes 240 for simplicity), and a set of evolution nodes 250-1 through 250-$q$ (referred to as evolution nodes 250 for simplicity).

The input nodes 210 may be or may include features extracted from a dataset for which internal component relationships are to be learned. The features represented by the input nodes 210 may be provided to the SOM 220 in a higher dimensionality format. As discussed further below, the features input to the SOM 220 via the input nodes 210 may be transformed into lower dimensionality representations via the SOM 220. More specifically, the features may include, but are not limited to, features indicating or otherwise representing characteristics of potential entities to be represented among the SOM 220 (i.e., entities whose connections may be modeled via connections between nodes in the SOM 220 and which may be learned using the SOM 220 and the GRN as described further below).

As a non-limiting example of features which may be utilized in accordance with the neurotransmitter connection identification as described further below with respect to FIG. 6, the input nodes 210 may include features extracted from phenotypic data, genotypic data, or both. More specifically, such non-limiting example features used for analyzing neuropeptide relationships, neurotransmitter relationships, hormone relationships, and the like. Such features may include, but are not limited to, amino acid composition features (e.g., a frequency of each amino acid in the peptide), physiochemical property features (e.g., attributes such as hydrophobicity, charge, molecular weight, combinations thereof, etc.), secondary structure prediction features (e.g., predicted structural features of an unidentified neuropeptide, neurotransmitter, or hormone), combinations thereof, portions thereof, and the like. Non-limiting example secondary structures may include, but are not limited to, alpha helices, beta sheets, turns, loops, and random coils.

Secondary structure features may be relevant to determining interactions because they relate to defining how a peptide interacts with receptors and other molecules, thereby influencing biological activity. More specifically, secondary structure features may determine how a peptide folds and what shape it takes, which in turn influences how the peptide interacts with receptors or other molecules. Accordingly, it has been identified that understanding relationships between secondary structure features and other features may aid in predicting activity of a peptide, which in turn may be utilized to design analogs for therapeutic purposes, elucidating the mechanism of action of the peptide within the nervous system, both, and the like. To this end, it has been further identified that the GRN architectures described herein such as the GRN architecture depicted in FIG. 2 may be particularly suitable for accurately and efficiently learning these interactions related to secondary structure features.

In various embodiments, the features provided via the input nodes 210 may be normalized and, in particular, normalized in order to ensure that the features contribute proportionally to the training of the SOM 220 (e.g., to ensure that each feature contributes equally to training as each other feature).

In an embodiment, the input nodes 210 may be realized via sets of nodes arranged in one or more neural networks (not depicted in FIG. 2). In particular, in an embodiment, the input nodes are realized using an adversarial network such as, but not limited to, a generative adversarial network (GAN). Such an adversarial network may include multiple neural networks which compete with each other.

In a GAN, a first neural network acts as a generator, and a second neural network acts as a discriminator, where the generator network is configured to generate fake examples and the discriminator network is configured to classify input examples as either real or fake, where the input examples include a mix of real examples and fake examples generated by the generator network. In this regard, the GAN acts using a supervised learning process where information about the examples that are either real (from a given domain of real data) or fake (generated by the generator network) is used to determine whether each example has been correctly classified by the discriminator network as real or fake. During training, examples may be generated and classified until the amount of false identifications by the discriminator reaches a predetermined threshold such as, but not limited to, 50% of examples classified incorrectly (i.e., the discriminator being fooled about half of the time). Once trained, the GAN may produce examples (e.g., examples from which features may be extracted and provided to the SOM 220 as discussed herein).

In an embodiment, the GRN architecture is realized using multiple adversarial networks. To this end, in such an embodiment, the GRN architecture may be realized using first and second GANs, with each GAN having a generator network and a discriminator network. In a further embodiment, the first GAN is used for generating and classifying implicit data, while the second GAN is used for generating and classifying explicit data. In this regard, it has been identified that using a combination of both explicit data (e.g., dominance as represent ed via time and frequency) as well as implicit data (e.g., evolution of internal components) may allow for unearthing hidden information such as the evolution of internal components, which in turn may provide a better understanding of complex interactions such as the role neuropeptides play in various biological functions. Features from both the implicit and explicit data examples may be provided for subsequent processing and utilized to learn dominance and the evolution of internal components as discussed below. Accordingly, it has further been identified that using multiple adversarial networks to generate a combination of implicit and explicit data examples may improve learning for the GRN architecture, which in turn may allow for more accurately identifying the existence and location of internal mechanisms such as, but not limited to, previously unidentified neuropeptides.

Features from the input nodes 210 are provided as inputs to the SOM 220. In an embodiment, the SOM 220 is a neural network which may be utilized for data visualization and dimensionality reduction. In a further embodiment, the SOM 220 uses an unsupervised competitive learning process in order to visualize high-dimensional data in a manner that can be represented via nodes during subsequent processing. Accordingly, integrating the SOM 220 as part of or otherwise with the GRN architecture depicted in FIG. 2 allows for condensing high-dimensional data in a manner which allows for unearthing activities of internal components or otherwise allows for effectively learning more complex internal relationships.

In an embodiment, each node of the SOM 220 represents an entity for which relationships are to be modeled. Nodes among the SOM 220 may be mapped to proximate nodes (e.g., using distance as calculated based on values representing properties of the respective entities), thereby forming clusters of nodes representing entities having similar properties. Accordingly, outputs of the SOM obtained via training of the SOM provides a basis for modeling potential relationships between such entities. These potential relationships may be further analyzed with respect to changes over time via a GRN (e.g., a GRN having dominance factor nodes, compounding change nodes, and evolution nodes) as discussed herein in order to effectively learn how the evolution of internal components affects these relationships, which in turn may allow for unearthing mechanisms behind these relationships.

A SOM may be utilized to transform nonlinear statistical relationships between high-dimensional data items into lower complexity geometric relationships which may be represented via a low-dimensional display. More specifically, a SOM can be utilized to visualize high-dimensional data in a two-dimensional (2D) space while preserving topological properties of the input space (i.e., the input space of the input features represented by the input nodes 210). As discussed herein, a SOM may be utilized in order to visualize relationships with complex interactions such as phenotypic and genotypic relationships.

In this regard, it has been identified that SOMs demonstrate beneficial properties for clustering, visualization, and pattern recognition tasks. Consequently, it has been identified that SOMs may be utilized in order to prepare data for processing via a GRN as described herein and, specifically, for efficiently preparing the data for such processing.

Using the SOM 220 as part of the GRN architecture therefore allows for learning and understanding these complex interactions by applying a GRN (e.g., a GRN including the nodes 230, 240, and 250 as depicted in FIG. 2) to data represented in the SOM 220.

The SOM 220 is trained using inputs provided via the input nodes 210. As discussed further below, during the training, the SOM 220 organizes nodes on a grid (e.g., a two-dimensional grid). Nodes of the SOM 220 associated with features representing similar properties are mapped to nearby nodes in the SOM 220, thereby forming clusters. These clusters may therefore allow for organizing the nodes in order to effectively represent potential relationships, and in particular to efficiently identify as many potentially relevant relationships as possible. In an embodiment, during training, weights of the nodes in the SOM 220 are adjusted in order to minimize the distances between input data and node weights. The node weights are adjusted iteratively until the SOM 220 stabilizes such that the stabilized SOM 220 represents a topologically organized structure of the input data. An example process which may be utilized to train the SOM 220 is described further below with respect to FIG. 5.

Outputs of the SOM 220 are input to a generative relational network (GRN). Such outputs may be or may include, but are not limited to, clusters identified based on proximity within the SOM 220. Moreover, new data and relationships may be input to the SOM 220 over time, thereby producing new outputs of the SOM to be input to the GRN. This may allow for continuously updating and refining the GRN over time based on incoming data and relationships, and in particular for continuously learning weights for machine learning models among the GRN based on changes in outputs of the SOM over time.

As depicted in FIG. 2, the GRN is made up of the dominance (D) factor nodes 230, the compounding change (C) nodes 240, and the evolution (E) nodes 250.

The dominance factor nodes 230 represent dominance factors which may influence the evolution of the ontology represented by the GRN architecture. The dominance factors may represent dominance of nodes which are mutually exclusive, that is, the dominance factor for a given first node as related to a given second node may represent a degree to which the dominance of the entity represented by the first node represses any influence of the entity represented by the second node. In an embodiment, each dominance factor is calculated as follows:

$$D(t)=\alpha*I(t)+\beta*F(t) \qquad \text{Equation 1}$$

In Equation 1, D(t) is the dominance factor at time t, I(t) is the intensity of changes at time t, F(t) is the frequency of changes up to time t, and α and β are weighting factors that determine the effects of intensity and frequency, respectively. While training the GRN, the values of α and β may be learned. Using dominance factors determined based on intensity and frequency of changes aids in effectively expressing factors which are relevant to the evolution of internal components, which in turn enables using machine learning to learn evolution of internal components over time. Each of the dominance factor nodes 230 may therefore be configured to determine a value for the dominance factor at time t using Equation 1.

Outputs of the dominance factor nodes 230 are input to the compounding change nodes 240, which represent compounding of anomalies over time which may influence the evolution of internal components. In an embodiment, each compounding change is calculated as follows:

$$C(t)=C(t-1)+D(t) \qquad \text{Equation 2}$$

In Equation 2, $C(t)$ is the compounding change up to time t, $C(t-1)$ is the compounding change up to time t−1, and $D(t)$ is the dominance factor at time t. Each of the compounding change nodes 240 may therefore be configured to determine a value for the compounding change at time t using Equation 2. Accordingly, the compounding change nodes 240 define compounding anomalies with respect to dominance and differences from prior changes over time.

Outputs of the compounding change nodes 240 are input to the evolution nodes 250, which represent the evolution of understanding of internal components of entities represented by nodes of the SOM 220. In an embodiment, the evolution represented by each evolution node 250 is calculated as follows:

$$E(t)=E(t-1)+\gamma^*C(t) \qquad \text{Equation 3}$$

In Equation 3, $E(t)$ is the evolution up to time t, $E(t-1)$ is the evolution up to time t−1, $C(t)$ is the compounding change up to time t, and $\gamma$ is a weight that determines the influence of compounded anomalies on evolution. While training the GRN, the value of $\gamma$ may be learned. Each of the evolution nodes 250 may therefore be configured to determine a value for the dominance factor at time t using Equation 3.

It should be noted that FIG. 2 depicts a particular GRN architecture according to at least some embodiments, but that various disclosed embodiments are not limited to the GRN architecture depicted in FIG. 2. Additional components may be incorporated into the GRN architecture without departing from the scope of at least some embodiments. Moreover, the SOM may be integrated in the GRN architecture with the GRN, or may be realized separately from the GRN architecture without departing from the scope of the disclosure.

A non-limiting example usage of the GRN architecture depicted in and described with respect to FIG. 2 is described further below with respect to FIG. 9.

Figure 3:
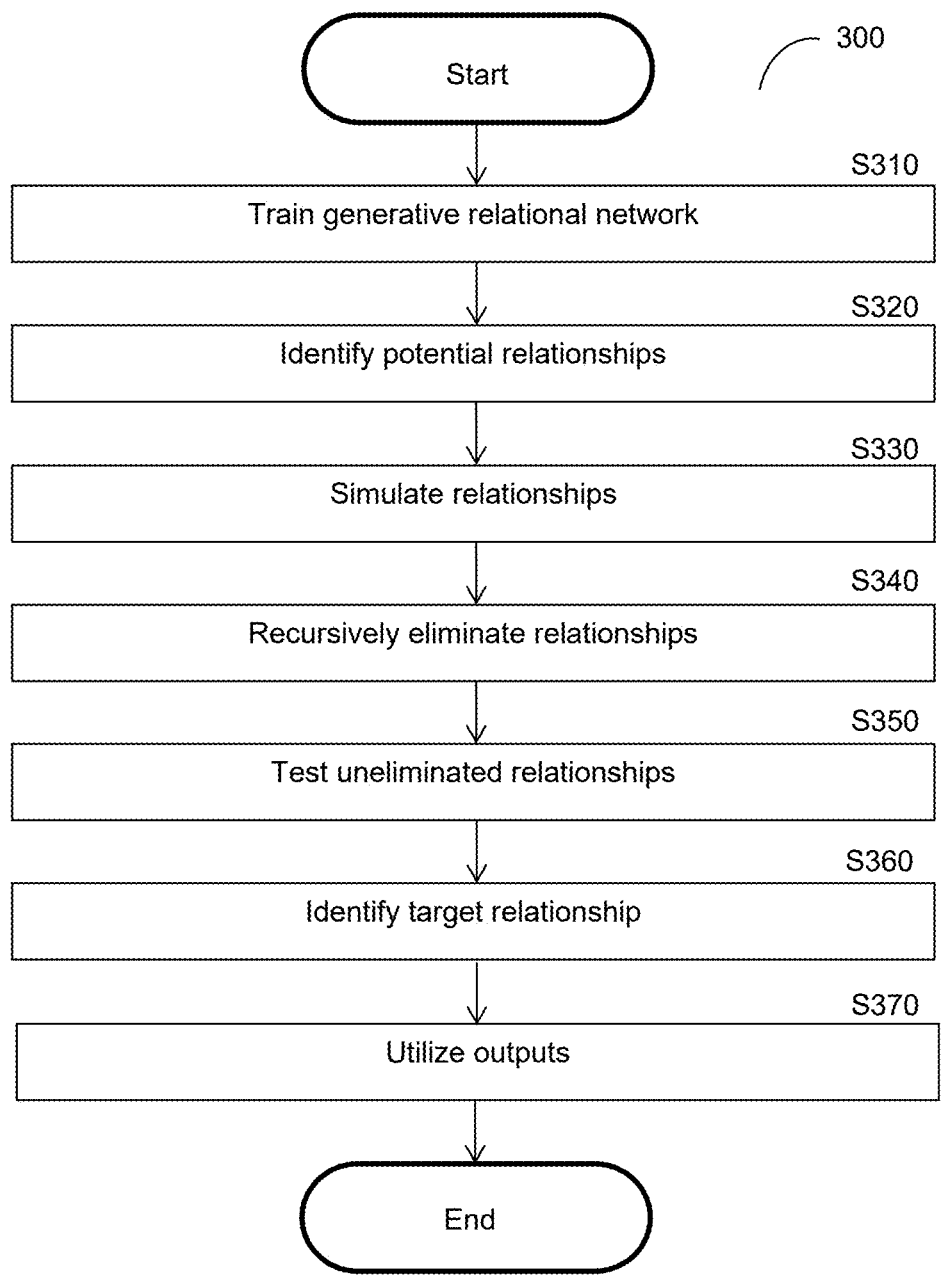
FIG. 3 is a flowchart illustrating a method for applying a generative relational network according to an embodiment.

FIG. 3 is a flowchart 300 illustrating a method for applying a generative relational network according to an embodiment. In an embodiment, the method is performed by the GRN manager 130, FIG. 1.

At optional S310, a generative relational network (GRN) may be trained. Alternatively, a pretrained generative relational network may be utilized.

The GRN includes multiple sets of nodes which can be utilized to understand the evolution of internal components among a modeled system including multiple entities. More specifically, in an embodiment, the GRN includes a set of dominance factor nodes, a set of compounding change nodes, and a set of anomaly nodes, for example as discussed above with respect to FIG. 2. Outputs from one set of nodes in the GRN may be input to the next set of nodes of the GRN in series. In a further embodiment, the GRN is trained based on outputs of a self-organizing map (SOM). In an embodiment, the GRN is trained as described further below with respect to FIG. 4.

At S320, potential relationships are identified between entities represented by nodes of the GRN. In an embodiment, the potential relationships are identified as potential interactions represented by activities involving two or more entities.

In an embodiment, identifying the potential relationships includes inferring potential unknown interactions. In a further embodiment, the potential unknown interactions are inferred by applying one or more machine learning models. Such machine learning models may be or may include a neural network such as a support vector machine.

In an embodiment, inferring the potential unknown interactions includes determining correlation coefficients for activity levels between different entities (e.g., different neuropeptides or other neurotransmitters). Alternatively or in combination, in an embodiment, network analysis algorithms or centrality measures may be utilized in order to identify potential hubs in the network or otherwise nodes with high centrality scores. Such high centrality nodes may be more likely to be relevant to unknown interactions and therefore indicative that the node has an unknown interaction. The result of such correlation or centrality analyses are inferred interactions (e.g., an interaction between entities indicated by a correlation coefficient between the entities above a threshold or an interaction with an entity indicated by a centrality score of a node representing the entity above a threshold).

At S330, relationships are simulated. More specifically, certain activities which may result in interactions between entities are simulated, thereby simulating relationships represented by potential interactions identified by simulating the activities. In an embodiment, a simulation machine learning model is applied to input data related to the entities represented in the GRN in order to generate parameters for the simulation.

At S340, relationships are eliminated. In an embodiment, eliminating the relationships includes analyzing results of the simulation in order to identify any expected reactions which would be observed if a relationship exists between a given pair of entities, and determining whether each expected reaction is demonstrated in the simulation results. If an expected reaction for a given pair of entities is not observed in the simulation results or otherwise if the simulation results lack the expected reaction for a potential relationship between a given pair of entities, then it may be determined that there is no relationship between those entities and any potential relationship between those entities may be eliminated. In some embodiments, the relationships may be eliminated with respect to location, that is, potential relationships may be defined based on locations between entities (e.g., edges between nodes in a graph), and eliminated potential relationships may be defined as a lack of a relationship at such a location.

In some embodiments, the relationships are recursively eliminated in a series of iterations. In each iteration, relationships are simulated, and relationships are eliminated. In a further embodiment, relationships may continue being recursively eliminated until, for example, no more relationships are eliminated during a given iteration.

At S350, the remaining relationships (i.e., the uneliminated relationships which remain after recursively eliminating the relationships) are tested. In an embodiment, testing the remaining potential locations includes testing the simulated activities in those locations. More specifically, the simulated activities may be tested with respect to the remaining locations in order to identify any interactions involving those potential locations.

At S360, a target relationship is identified among the remaining relationships based on results of the testing. More specifically, in an embodiment, a target interaction which might be indicative of the target relationship is identified based on the testing of the remaining relationships. When such a target interaction is found, the target relationship may be identified with respect to that target interaction.

At optional S370, outputs are utilized. Using the outputs may include, but is not limited to, identifying the existence of an entity (e.g., a neurotransmitter hypothesized to have the target relationship with another neurotransmitter or other entity), treating a patient based on the target relationship (e.g., applying a treatment targeting the interaction of the target relationship), or otherwise using the identified relationship.

Figure 4:
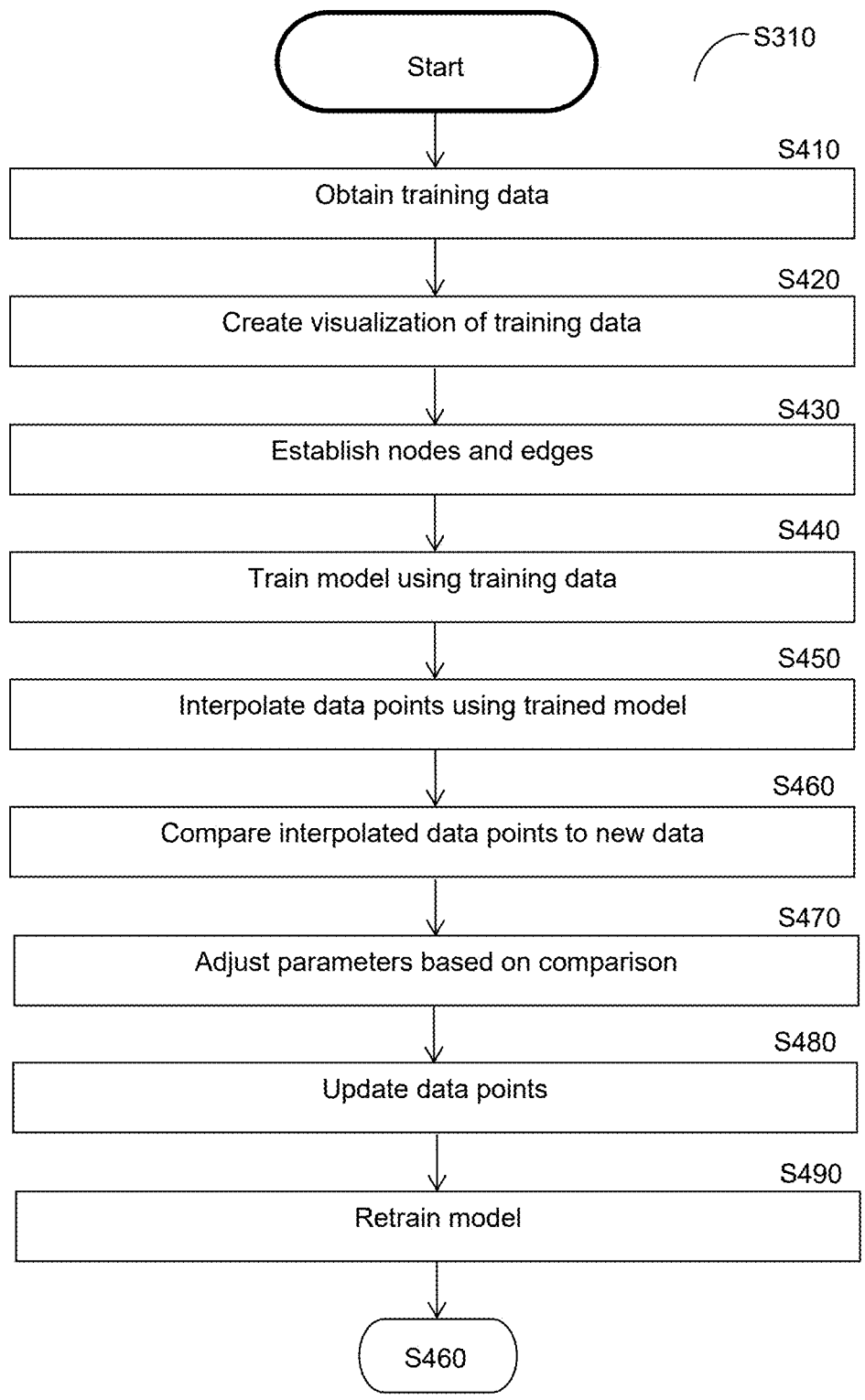
FIG. 4 is a flowchart illustrating a method for training a generative relational network according to an embodiment.

FIG. 4 is a flowchart S310 illustrating a method for training a generative relational network according to an embodiment.

At S410, training data is obtained. The training data may be or may include various data points representing respective properties of entities whose relationships are to be modeled in order to learn the evolution of internal mechanisms or other components which affect behavior of those entities as discussed herein. When the entities are neurotransmitters and neuropeptides, non-limiting example types of data which may be obtained include concentrations, receptors, known interactions, and effects on certain physiological functions.

At S420, a visualization of the training data is created. In an embodiment, the visualization of the training data is created using a self-organizing map (SOM). In a further embodiment, the SOM is an artificial neural network having nodes, where the nodes may represent respective entities. The SOM may generate the visualization in the form of a map which is a lower-dimensional representation of the training data (i.e., has a lower dimensionality than the training data). Each node may have a corresponding weight representing a position of the node in the input space, where the weight may be realized as a weight vector. Accordingly, the weights of the nodes collectively define the visualization of the training data.

At S430, edges are established between nodes among the SOM. The edges represent relationships between the entities represented by respective pairs of nodes connected by the edges. In an embodiment, the edges are established based on proximity between nodes, for example, by connecting nodes which are clustered together in the SOM via edges. As discussed herein, such clustering may be performed based on distances between nodes (e.g., based on distances calculated between weight vectors of respective nodes).

At S440, models of a GRN architecture are trained using the training data. In an embodiment, S440 includes applying models of the GRN architecture in a training mode in order to learn weights for those models. More specifically, a SOM may be trained, and the outputs of the trained SOM may be utilized to learn weights for sets of nodes of a GRN (with each node corresponding to a respective model). For example, weights may be determined for one or more of dominance factor nodes, compounding change nodes, and evolution nodes.

At S450, data points are interpolated using the trained models. The data points may be interpolated in order to fill in missing or otherwise unknown data points, i.e., data points which are missing among the training data. To this end, in an embodiment, S450 includes applying an interpolation model designed to interpolate data points based on input data. The interpolated data points, also referred to as interpolants, are estimated values that may bridge gaps in a dataset. The interpolated data points may be created in order to fill gaps in the dataset.

The interpolation model may utilize one or more interpolation methods such as, but not limited to, linear interpolation, polynomial interpolation, spline methods kriging, combinations thereof, and the like. The interpolation methods utilized may be selected, for example, based on the nature of the data points, any known underlying patterns, and otherwise depending on the use case. In some embodiments, the interpolation model is a pretrained model configured to interpolate in accordance with one or more predetermined interpolation methods, and may be selected based on the use case.

At S460, the interpolated data points are compared to new data (e.g., newly received or otherwise obtained data, or a subset of the original dataset such as a subset which was excluded from use during the original training). The comparison may be performed in order to determine an error value, which may be utilized to determine how to update the model.

In this regard, it is noted that, while interpolants can provide relevant contextual data points for exposing patterns or otherwise better representing the underlying information, inaccurate interpolants can actually impede model accuracy. Accordingly, validating the interpolated data points, for example by comparing the interpolated data points to real data points and determining error values, may allow for mitigating the negative impacts on model performance caused by improper interpolants. That is, if the interpolants generally are close to actual values, then confidence in the interpolation model is increased, and the likelihood that using interpolated data points to train the other model is reduced.

At S470, parameters of the models are adjusted based on the comparison. More specifically, the parameters are updated based on the error such that subsequent iterations should have lower error.

At S480, the data points are updated with at least some of the interpolated data points. In some embodiments, interpolated data points having error values below a predetermined threshold may be added to a training data set, while interpolated data points having error values above the predetermined threshold are not added to the training data set.

In some embodiments, the interpolation model may be iteratively refined by determining new interpolated data points, comparing those newly interpolated data points to other new data, and updating the training data set with more interpolated data points. To this end, in such embodiments, any or all of steps S450 through S480 may be iteratively performed, for example, until a threshold number of iterations has been performed or a threshold performance (e.g., error rate below a predetermined threshold) has been reached.

At S490, the model is retrained using the training data set including the interpolated data points, thereby resulting in a refined model which has been retrained using interpolants. As noted above, using the interpolants fills gaps in data such that the resulting refined model is trained on a more robust set of data.

In an embodiment, after S490, execution continues with S450 where the retrained model is applied in order to interpolate data points again. The newly interpreted data points may then be compared to new incoming data at S460 and utilized to ultimately retrain the model again at S490. Such an embodiment may allow for continuously, repeatedly, or otherwise iteratively improving the model. Moreover, during subsequent iterations as more data becomes available, interpolated data points may be replaced with new actual data points, thereby causing the updated ontology to rely less on interpolants which inherently carry more uncertainty than actual data points. That is, the interpolants may be utilized to improve the model short term, and ultimately end up being replaced with real data points to further improve the model longer term.

In this regard, it has been identified that interpolants may be relevant for improving data quality in use cases such as, but not limited to, time-series forecasting and regression analysis. In particular, interpolants may allow for providing a continuous or otherwise more complete representation of information expressed in the data points, which aids in improving accuracy for time-series forecasting and regression analysis. Additionally, interpolation may allow for determining impacts of certain changes more granularly than using more sparse datasets. As a non-limiting example, if a sudden spike or drop is observed in a time-series dataset, interpolants may aid in learning a gradient or rate of change between known data points, which in turn may add context regarding potential external factors or anomalies. Further, a technical challenge with machine learning models is overfitting, particularly when using sparse datasets. By using interpolants, or interpolated data points, to fill in missing or otherwise unknown data, the dataset becomes more robust, thereby allowing for improving model accuracy.

It has further been identified that, for datasets with a temporal or spatial component, interpolants may provide additional insights into trends, patterns, and behaviors which might not otherwise be recognizable using sparse datasets or otherwise when at least some data is missing. As a non-limiting example, for climate data analysis, interpolation may aid in understanding temperature trends when temperature measurements are missing or otherwise unavailable for certain days. Accordingly, using interpolants as described herein may allow for unearthing new trends and patterns when applied to at least some use cases. Moreover, interpolants may aid in determining inferences about unobserved or unmeasured phenomena.

Figure 5:
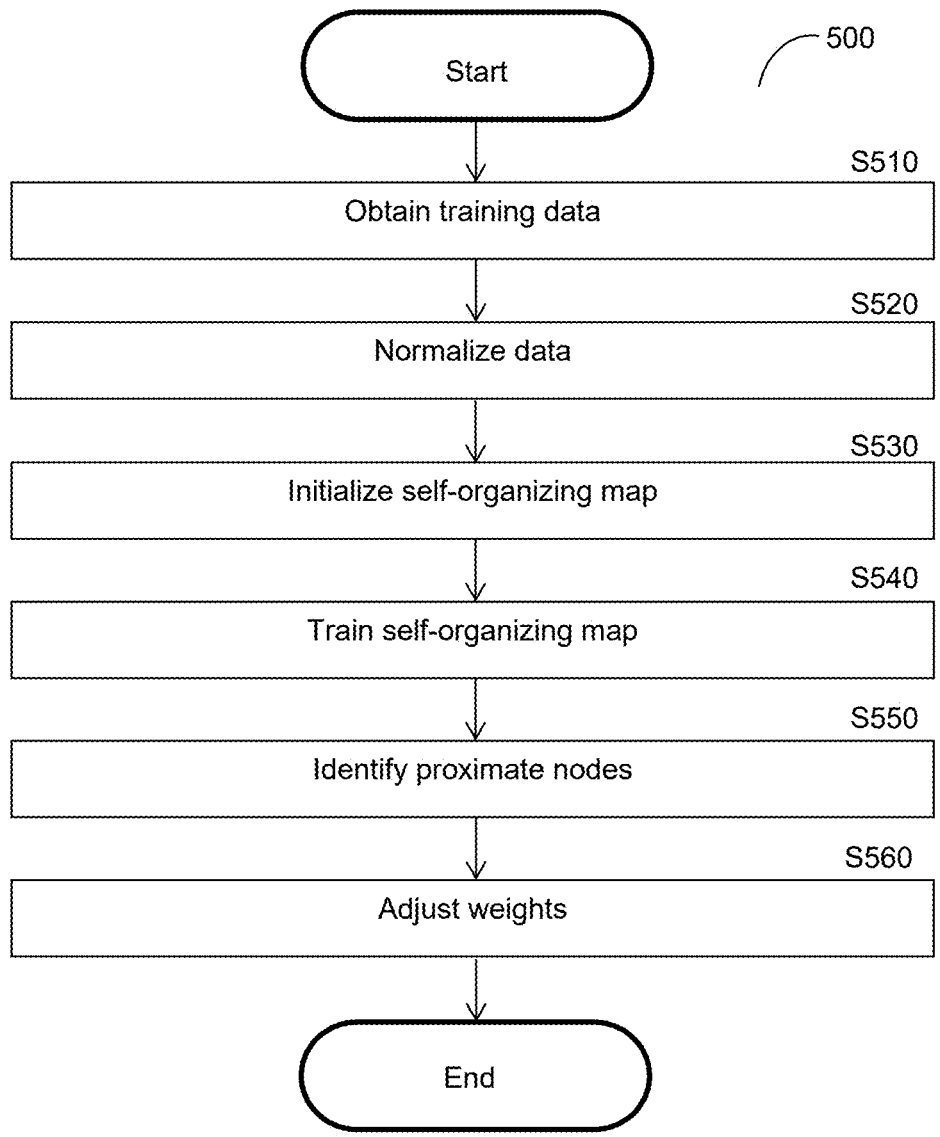
FIG. 5 is a flowchart illustrating a method for training a self-organizing map for use in applying a generative relational network according to an embodiment.

FIG. 5 is a flowchart 500 illustrating a method for training a self-organizing map for use in applying a generative relational network according to an embodiment. In an embodiment, the method is performed by the GRN manager 130, FIG. 1.

At S510, training data is obtained. The training data may be or may include, but is not limited to, data indicating properties of various entities. As discussed herein, similarities in such properties may be utilized by a self-organizing map in order to organize the map via clustering, thereby allowing for identifying entities that demonstrate similarities with respect to the properties. In an embodiment, the training data is realized as a set of training feature vectors, where each feature vector includes a set of values corresponding to respective features and representing attributes of different entities to be represented among the self-organizing map.

In a non-limiting example biological use case where the entities are or include neuropeptides, neurotransmitters, or hormones, such data may include features representing attributes such as amino acid composition (e.g., frequencies of different amino acids in peptides), physiochemical properties (e.g., hydrophobicity, charge, molecular weight, etc.), secondary structure predictions (e.g., predictions for alpha helices, beta sheets, turns and loops, random coils, etc.), combinations thereof, and the like.

At S520, the training data is normalized. In an embodiment, the data is normalized in order to ensure proportional contributions of features. In a further embodiment, the data is normalized such that each feature contributes equally to the training as each other feature. To this end, the data may be normalized with respect to scale such that all features among the data are represented via the same scale.

In this regard, it is noted that self-organizing maps are sensitive to input data scale. Accordingly, normalizing the data with respect to scale allows for improving the self-organizing map, which in turn allows for improving a GRN applied based on the self-organizing map.

At S530, a self-organizing map (SOM) is initialized. To this end, initializing the SOM may include, but is not limited to, initializing parameters of the SOM (e.g., dimensions of the SOM or grid size, learning rate, sigma value, number of iterations to use for training etc.), initializing weights of the SOM, or both. In an embodiment, the SOM is initialized with randomized weights. In another embodiment, the parameters of the SOM may be initialized using respective predetermined values for the parameters.

At S540, the SOM is trained using the training data. In an embodiment, training the SOM includes providing feature vectors as inputs to the SOM. The SOM may be realized via a set of nodes and edges connecting between the nodes. The nodes may represent components whose relationships are to be learned such that using the SOM allows for efficiently and effectively visualizing potential relationships between such components which may be analyzed using a GRN during subsequent processing.

In an embodiment, the SOM is an artificial neural network configured to operate in a training mode and a mapping mode. In the training mode, the SOM generates a lower-dimensional representation of input data as a map. In the mapping mode, the SOM classifiers additional input data using the resulting map. Accordingly, training the SOM allows for representing an input space with "p" dimensions (where p is an integer having a value of 1 or greater) using a map space with a lower number of dimensions (e.g., two dimensions). The map space includes nodes (also referred to as neurons), where each node is associated with a corresponding weight (e.g., a weight vector). The weight of each node represents the position of the node in the input space. Once trained, the resulting map may be utilized to classify additional observations for the input space by identifying a node with the closest weight vector to an input space vector of each additional observation.

During the training, the SOM organizes data points on a grid (e.g., a two-dimensional grid). Nodes of the SOM associated with data points representing similar properties are mapped to nearby nodes in the SOM, thereby forming clusters. These clusters may therefore allow for organizing the nodes in order to effectively represent potential relationships, and in particular to efficiently identify as many potentially relevant relationships as possible. In an embodiment, during training, weights of the nodes in the SOM are adjusted in order to minimize the distances between input data and node weights. The node weights are adjusted iteratively until the SOM stabilizes such that the stabilized SOM represents a topologically organized structure of the input data.

Once the SOM is trained, it can be used to identify clusters of entities with similar properties. As a non-limiting example, similar neuropeptides, neurotransmitters, or hormones may be identified based on clusters of entities representing neuropeptides, neurotransmitters, or hormones, respectively. Such clusters may provide insights into functional roles of the entities represented therein, or otherwise may provide insights into potential interactions of these entities. That is, the clusters may be indicative of similar properties (e.g., similar biological functions or structural characteristics) of the entities represented by nodes (e.g., neuropeptides, neurotransmitters, or hormones) such that the clusters may provide insights into different entities which, for example, behave or are structured similarly.

The resulting clusters may further be analyzed in order to understand underlying characteristics of each group (i.e., each group of entities represented by a given cluster). As non-limiting examples, the clusters may be analyzed for purposes such as functional annotation, pathway analysis, novelty detection, and the like.

In this regard, it has been identified that SOMs may be utilized to classify entities such as neuropeptides, neurotransmitters, and hormones into different families based on characteristics such as sequences and structural features, which in turn may help to predict their functions since sequence and structure features play a role in causing certain functions. Accordingly, it has been identified that, by clustering neuropeptides, neurotransmitters, and hormones with known functions, SOMs may be utilized to help infer the functions of uncharacterized neuropeptides, neurotransmitters, and hormones (i.e., entities with unknown functions) that are clustered together with entities whose functions are known. Moreover, it has been identified that SOMs may be useful for learning the evolutionary relationships between neuropeptides, neurotransmitters, and hormones. More specifically, by clustering such entities based on sequence similarity and other features which may be predictive of function, interactions between them may be identified in order to better understand relationships therein, which may allow for more granular understanding of the mechanisms behind them. This, in turn, allows for more accurately modeling behavior of these entities, which in turn may be utilized to better identify entities which play pivotal roles in certain functions and may therefore enable targeting these pivotal entities in order to improve treatment or other uses of the identification.

At S550, proximate nodes are identified based on proximity of nodes to each other within the SOM. In an embodiment, for each data point among the inputs to the SOM, a closest node within the SOM is identified. In a further embodiment, identifying the closest node for a given data point includes calculating a distance (e.g., a Euclidean distance) between a node associated with the data point and other nodes (e.g., nodes connected to the node associated with that data point within the SOM). The result is identifying a closest node as a proximate node for each data point.

At S560, weights of the SOM are adjusted based on the identified proximate node for each data point. More specifically, in an embodiment, for each data point, a weight of the closest node for the data point is adjusted in order to move the closest node for the data point closer to a node associated with the data point within the SOM. In a further embodiment, a weight of each neighbor of the closest node for each data point may also be adjusted in order to move those neighbors closer to a node associated with the data point within the SOM. In some embodiments, the weights adjusted at S560 may be adjusted using predetermined values, and may be adjusted by either increasing or decreasing the weights depending on whether each weight being adjusted is below or above, respectively, a weight of a node associated with the data point. The result of such adjustment may be a SOM which has been tuned to have more pronounced clusters, which may improve accuracy during subsequent processing.

Figure 6:
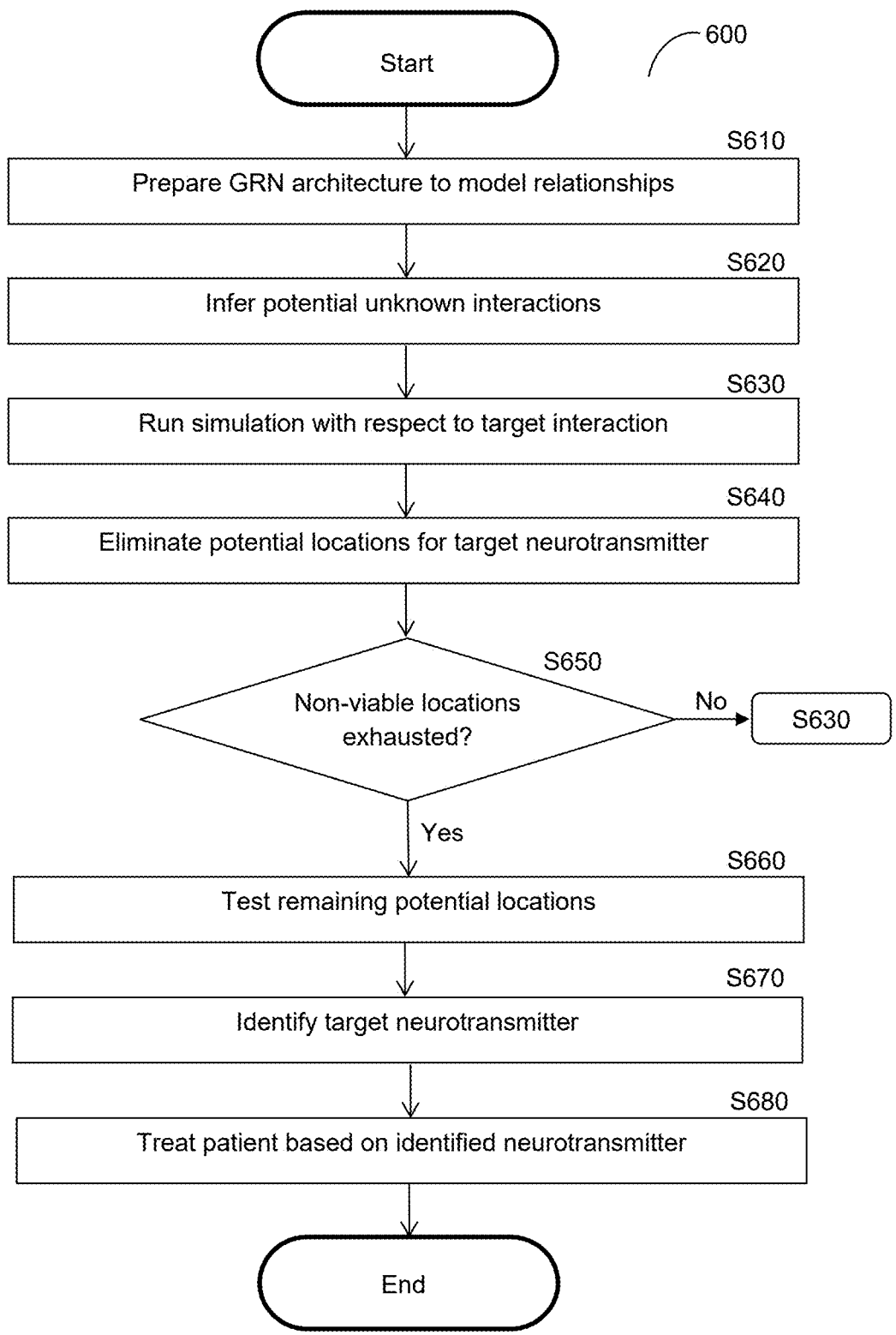
FIG. 6 is a flowchart illustrating a method for utilizing a generative relational network in order to identify connecting neurotransmitters according to an embodiment.

FIG. 6 is a flowchart 600 illustrating a method for utilizing a generative relational network in order to identify connecting neurotransmitters according to an embodiment. In an embodiment, the method is performed by the GRN manager 130, FIG. 1.

At S610, a generative relational network (GRN) architecture is prepared such that the GRN is adapted to model relationships between neurotransmitters. In an embodiment, S610 includes applying the GRN in order to create such a model of relationships between neurotransmitters.

In an embodiment, the GRN architecture has a GRN including multiple sets of nodes. In a further embodiment, such sets of nodes include a set of dominance factor nodes, a set of compounding change nodes, and a set of evolution nodes as discussed above with respect to FIG. 2. In yet a further embodiment, the GRN architecture further has a self-organizing map (SOM) used to cluster nodes representing the neurotransmitters.

In an embodiment, the chemical and mathematical relationships between the neurotransmitters are provided to the system (e.g., the GRN manager 130) utilizing the GRN architecture. To this end, any known relationships between neurotransmitters may be provided to the system for modeling. In a further embodiment, the GRN is further configured with the extent of any unknown factors (i.e., factors which are known or suspected to exist but for which the actual effects or mechanisms of such factors are unknown).

At S620, potential unknown interactions are inferred. In an embodiment, the potential unknown interactions are inferred by applying one or more machine learning models. In a further embodiment, the machine learning models include a support vector machine or other neural network trained using training data representing known interactions. Such networks trained on known interactions may then be applied to input data in order to infer potential interactions among entities represented in the input data. Correctional analysis network analysis, and computational methods may be additionally used to infer the potential unknown interactions.

In an embodiment, inferring the potential unknown interactions includes correlating between activity levels of different entities (e.g., different neuropeptides or other neurotransmitters). In a further embodiment, correlation coefficients may be determined for activity levels between entities, where higher correlation coefficients may indicate potential interactions. Alternatively or in combination, in an embodiment, network analysis algorithms or centrality measures may be utilized in order to identify potential hubs in the network or otherwise nodes with high centrality scores. Such high centrality nodes may be more likely to be relevant to unknown interactions and therefore indicative that the node has an unknown interaction.

At S630, a simulation is run with respect to a target interaction. More specifically, effects of one of the potential unknown interactions acting as the target interaction for a given iteration are simulated. The simulation may include, but is not limited to, one or more simulated activities which may result in certain interactions.

In an embodiment, the simulation is run based on a simulation model. To this end, running the simulation may include applying the simulation model in order to determine one or more inputs for the simulation, and running the simulation using those inputs. In a further embodiment, the simulation model is a machine learning model trained on data relevant to the interactions. Such data may depend on the use case. As a non-limiting example for a medical use case, such data may include extracted and de-identified (i.e., having personally identifiable information removed) versions of data including electronic health records, electron microscopy derived data, electroencephalogram (EEG) results, quantitative electroencephalography (QEEG) results, magnetic resonance imaging (MRI) results, functional MRI (fMRI), X-Ray results, computed axial tomography (CAT) scan results, repetitive transcranial magnetic stimulation (rTMS) results, deep brain stimulation (DBS) results, position emission tomography (PET) results, genetic analysis readings, genomic analysis results, combinations thereof, portions thereof, and the like. In a further embodiment, any of this data may be obtained via computer vision by analyzing images from which this data may be derived.

In a non-limiting example medical use case where interactions of internal components in relation to a given disease state are to be analyzed, running the simulation may include selecting a disease state with known symptoms but idiopathic etiology. The simulation may then be performed in an attempt to replicate the biological processes which occur as a result of at least the target interaction while accounting for parameters representing symptoms or other effects of the disease state. As a non-limiting example, for a target interaction of a hypothesized "Neuropeptide X" (NX, a neurotransmitter that is hypothesized to have certain interactions but which has not been observed engaging in such interactions), biological processes which occur due to mechanisms of a G-coupled protein receptor in relation to NX, accounting for the hypothesized action of NX of the target interaction may be simulated.

At S640, potential locations for a target neurotransmitter are eliminated based on results of the simulation. In an embodiment, S640 may include analyzing the simulation results to identify any expected reactions which would result from the target interaction with the target neurotransmitter, for example, expected neuropeptide reactions. More specifically, such expected reactions may be defined based on a type of reaction as well as relative locations where the reaction is expected to have effect (e.g., expected locations of neurotransmitters relative to the target neurotransmitter, assuming that the target neurotransmitter exists). Based on the expected reactions, potential locations where the target neurotransmitter could exist may be eliminated.

Alternatively or in combination, characteristics or features which are unexpected for the target neurotransmitter (i.e., which the target neurotransmitter could not possess) may be checked against the simulation results in order to determine locations of neurotransmitters having these unexpected characteristics or features. These locations may then be eliminated from being potential locations for the target neurotransmitter.

At S650 it is checked if all impossible or otherwise non-viable locations have been exhausted and, if so, execution continues with S660; otherwise, execution continues with S630 where another simulation is run. In an embodiment, all non-viable locations may be determined to be exhausted when an iteration of simulation results in failing to eliminate any potential locations at S640.

At S660, remaining potential locations are tested. In an embodiment, testing the remaining potential locations includes testing the simulated activities in those locations. More specifically, the simulated activities may be tested with respect to the remaining locations in order to identify any interactions involving those potential locations.

In some embodiments, the simulation model may be iteratively refined using new data and validating inferred interactions through experimental or observational studies. To this end, in such embodiments, execution may continue with S620 when new data is received.

At S670, a target neurotransmitter is identified. More specifically, the interactions identified during testing of the remaining potential locations may be analyzed in order to determine one of the interactions as being the target interaction which is hypothesized to be caused by the target neurotransmitter. When an interaction has been determined to be the target interaction, the potential location involved in that interaction may be determined as the location of the target neurotransmitter, and the target neurotransmitter may be identified with respect to that location (i.e., as the neurotransmitter at that location).

At optional S680, a patient is treated based on the identified neurotransmitter. In an embodiment, treating the patient includes applying or prescribing a treatment targeting the identified neurotransmitter. More specifically, in a further embodiment, treating the patient may include causing a drug designed to either mimic or block the neurotransmitter in order to provide or prevent effects of the neurotransmitter, respectively.

As a non-limiting example application of the process of FIG. 6, an example application is utilized to identify potential interactions between neurotransmitters dopamine, oxytocin, and serotonin. Data on concentrations, receptors, and known interactions among the neurotransmitters is collected. An adjacency matrix is generated and populated with the collected data. Known interactions may be represented by nonzero values, while lack of known interactions may be represented by zero values in the adjacency matrix. A correlation is determined between dopamine and serotonin. Centrality of dopamine, oxytocin, and serotonin within the network is analyzed. A trained machine learning model is applied in order to predict if dopamine and serotonin might interact. Effects of potential dopamine-serotonin interactions are simulated, and the simulation results may be validated via external studies. The adjacency matrix may be updated based on the simulation results, and the process of updating the adjacency matrix may be repeated.

By iteratively refining the adjacency matrix, the chemical composition of Neuropeptide X (also referred to as NX, a hypothesized neurotransmitter) may be identified based on potential locations and functions. The chemical composition may be hypothesized by examining the characteristics of well-known neuropeptides, for example using a k-nearest neighbor (KNN) process. Such neuropeptides may include chains of amino acids with certain sequences which allow them to bind to their receptors in order to carry out their functions (e.g., biological functions). Hypothesized values of NX's chemical composition may include, but are not limited to, a range of predicted potential lengths (e.g., between 3 and 50 amino acids in length).

Using the representation of evolution which may be realized using a GRN architecture in accordance with various disclosed embodiments, the evolution of interactions between NX with oxytocin and dopamine may be modeled based on anomalies or other notable changes in their interactions. Accordingly, the models of the GRN may aid in predicting how the role of NX may change under different physiological or pathological conditions. The consideration of time and frequency in evolution (e.g., as considerations for dominant factors as discussed herein) allows for understanding how the effects of NX may change over time and with varying frequencies of activation, which in turn helps to model dynamic interactions between NX, oxytocin, and dopamine across different temporal scales. Moreover, the GRN as discussed herein may allow for integrating phenotypic observations (e.g., behavioral changes caused by NX) with genotypic data (e.g., receptor interactions, gene expression profiles, etc.). This integration may therefore allow for revealing how the effects of NX manifest at the behavioral level and their roots in molecular mechanisms, thereby offering a more comprehensive understanding of its role.

A GRN being used to analyze NX may be iteratively refined in order to continuously update the understanding of NX as new data becomes available. This allows for improving the modeling of NX, which in turn may allow for more accurately or granularly identifying NX (e.g., more accurately or granularly identifying a location of NX), which in turn allows for more accurate or more precise actions based on the identification of NX (e.g., better targeting treatments for treating patients via use of NX).

Moreover, using the algorithmic representation offered by GRN allows for exploring how the role of NX might evolve in response to physiological changes or disease states. As a non-limiting example, for neurodegenerative diseases, NX might adapt its interactions with oxytocin and dopamine in order to compensate for neuronal loss or dysfunction, which in turn may be utilized to identify potential therapeutic targets.

Various non-limiting examples of potential roles the hypothesized NX could play which may be identified by identifying NX as a target neurotransmitter using the process of FIG. 6.

Hypothalamus: The hypothalamus is a key center for neuropeptide activity, regulating autonomic functions and hormone release. NX could influence body temperature, hunger, thirst, and circadian rhythms in the hypothalamus.

Pituitary Gland: As a central hub for hormone release, NX could modulate the secretion of hormones that affect peripheral functions, like growth hormone or adrenocorticotropic hormone (ACTH).

Brainstem: This region controls autonomic functions such as heart rate and respiration. NX might play a role in these processes by interacting with brainstem nuclei.

Autonomic Nervous System (ANS): Sympathetic Ganglia: NX could be involved in the regulation of sympathetic activities like vasoconstriction, heart rate increase, and stress responses.

Parasympathetic Ganglia: NX might modulate functions such as salivation, digestion, and heart rate reduction.

Peripheral Nervous System (PNS): Peripheral Nerve Endings: NX could be found at nerve terminals in the periphery, modulating pain signals, sensory inputs, or motor outputs.

Autonomic Nerve Fibers: In the PNS, NX might influence the autonomic fibers that extend to various organs and tissues.

Cardiovascular System: Blood Vessels: NX could be involved in vasodilation or vasoconstriction, similar to neuropeptides like Neuropeptide Y (NPY) or Substance P.

Heart: NX might play a role in modulating heart rate and myocardial contraction, influencing cardiac output and blood pressure.

Gastrointestinal Tract: Enteric Nervous System: Often called the "second brain," the enteric system controls gastrointestinal functions. NX could affect motility, secretion, and local blood flow.

Gastrointestinal Mucosa: NX might be involved in regulating digestive enzymes and absorption processes.

Respiratory System: Airways: NX could modulate airway constriction and dilation, impacting conditions like asthma or bronchoconstriction.

Respiratory Centers: Located in the brainstem, NX might influence respiratory rate and depth.

Immune System: Immune Cells: NX might interact with immune cells to modulate inflammatory responses or the immune system's interaction with the nervous system.

Lymphoid Organs: NX could be involved in regulating immune responses in organs like the spleen and lymph nodes.

Skin and Sensory Organs: Dermal Nerve Endings: NX might affect sensory perception, including pain, temperature, and touch.

Eyes and Ears: NX could influence sensory processing in the retina or auditory system.

Endocrine System: Adrenal Glands: Given their role in releasing stress hormones like adrenaline, NX might modulate these responses.

Pancreas: NX could affect the release of insulin or glucagon, influencing blood sugar regulation.

Reproductive System: Reproductive Organs: NX might influence functions in the reproductive organs, such as the ovaries or testes, affecting hormone release and reproductive processes.

Uterus and Prostate: NX could modulate smooth muscle contraction or glandular secretions in these organs.

Various non-limiting example potential amino acid structures for NX follow. Each of the following sequences is designed to include aromatic and positively charged residues, thereby enhancing the likelihood of interaction with receptors associated with dopamine, oxytocin, serotonin, combinations thereof, and the like. Moreover, various sequences among the following sequences were designed to improve peptide stability, flexibility, both, and the like. These potential amino acid structures may be analyzed using a GRN architecture as described herein in order to identify which (if any) of these structures belong to NX.

In the examples that follow, W represents Tryptophan, Y represents Tyrosine, R represents Arginine, C represents Cysteine, K represents Lysine, A represents Alanine, V represents Valine, P represents Proline, G represents Glycine, F represents Phenylalanine, T represents Threonine, L represents Leucine, Q represents Glutamine, and S represents Serine.

A first non-limiting example structure is WYRCRYKAVPG.

A second non-limiting example structure is WYCRFKTVLGP.

A third non-limiting example structure is WYRCKRLGAVP.

A fourth non-limiting example structure is WYCRFRLTVSP.

A fifth non-limiting example structure is WYRCRKVSGFP.

A sixth non-limiting example structure is WYRCKRLGAVP.

A seventh non-limiting example structure is WYQCKRFVSGP.

An eighth non-limiting example structure is YWKRCKAVFSP.

A ninth non-limiting example structure is WYCRLKTVGSP.

A tenth non-limiting example structure is WFRCKYSLVGP.

An eleventh non-limiting example structure is WYRCKAFVSLP.

A twelfth non-limiting example structure is WYCRKFSGVPL.

A thirteenth non-limiting example structure is YWCRKTFVSLG.

A fourteenth non-limiting example structure is WYKRCFSGTVP.

Figure 7:
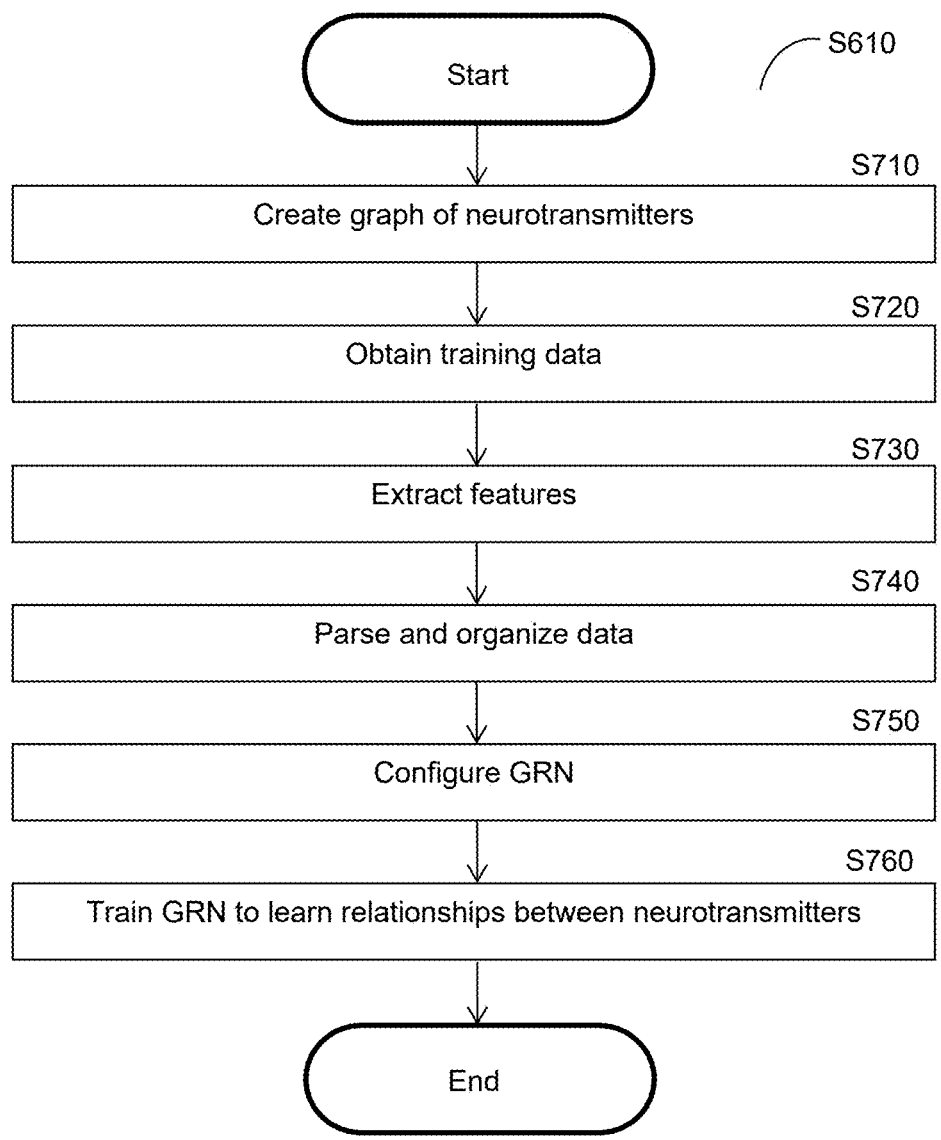
FIG. 7 is a flowchart illustrating a method for preparing a generative relational network for neurotransmitter identification according to an embodiment.

FIG. 7 is a flowchart S610 illustrating a method for preparing a generative relational network for neurotransmitter identification according to an embodiment.

At S710, a graph of neurotransmitters is created. The graph may be realized using a set of nodes and edges between nodes, with nodes representing neuropeptides or other neurotransmitters (e.g., dopamine, oxytocin, serotonin, etc.) and edges representing potential interactions or other relationships between neurotransmitters. The edges may be initially configured based on predetermined known interactions between neurotransmitters.

In some embodiments, the graph may be expressed mathematically as a weighted adjacency matrix with values representing the strength or presence of interactions between pairs of nodes. To this end, the edges may have weights representing these strengths or presences of interactions. The adjacency matrix may be updated over time with new data when the process of preparing the generative relational network is iteratively performed.

At S720, training data is obtained. The training data may include, but is not limited to, data indicating properties of neurotransmitters, receptors of neurotransmitters, binding affinities of neurotransmitters, the known interactions, pathways among neurotransmitters, physiological effects and responses, and the like.

At S730, features are extracted. Non-limiting example features may include amino acid compositions, sequences, both, and the like. The features may be normalized or otherwise transformed for subsequent use, for example by normalizing scale of the extracted features when the features are extracted from disparate data sets. In an embodiment, extracting the features includes performing visual analysis on images.

At S740, the training data is parsed and organized.

At S750, a generative relational network (GRN) is configured. In an embodiment, the GRN is configured such that the GRN models connections or relationships between entities represented by nodes (e.g., nodes of a self-organizing map as described herein). In a further embodiment, the GRN includes multiple sets of nodes, with each node corresponding to a respective machine learning model and is used to represent a value for a respective factor (e.g., a dominance factor, compounding changes, or evolution). In yet a further embodiment, the GRN is configured with a set of dominance factor nodes which provide outputs to be used as inputs to a set of compounding change nodes, where the set of compounding change nodes provide outputs to be used as inputs to a set of evolution nodes, for example as discussed further above with respect to FIG. 2. The GRN may be configured to receive inputs which have been organized and clustered by a self-organizing map as discussed herein. To this end, the GRN may be configured to accept inputs using a dimensionality corresponding to a dimensionality of outputs of the SOM.

At S760, the GRN is trained to learn relationships between neurotransmitters. The resulting GRN may then be applied in order to detect relationships between neurotransmitters in order to identify target neurotransmitters as described herein, for example with respect to FIG. 6. In an embodiment, training the GRN may include providing training input features (e.g., in the form of input feature vectors) to a self-organizing map (e.g., the SOM 220, FIG. 2), and outputs of the SOM may be utilized to organize training inputs to nodes of the GRN, thereby training the GRN. In some embodiments, the GRN may be trained as discussed further above with respect to FIG. 4.

Figure 8:
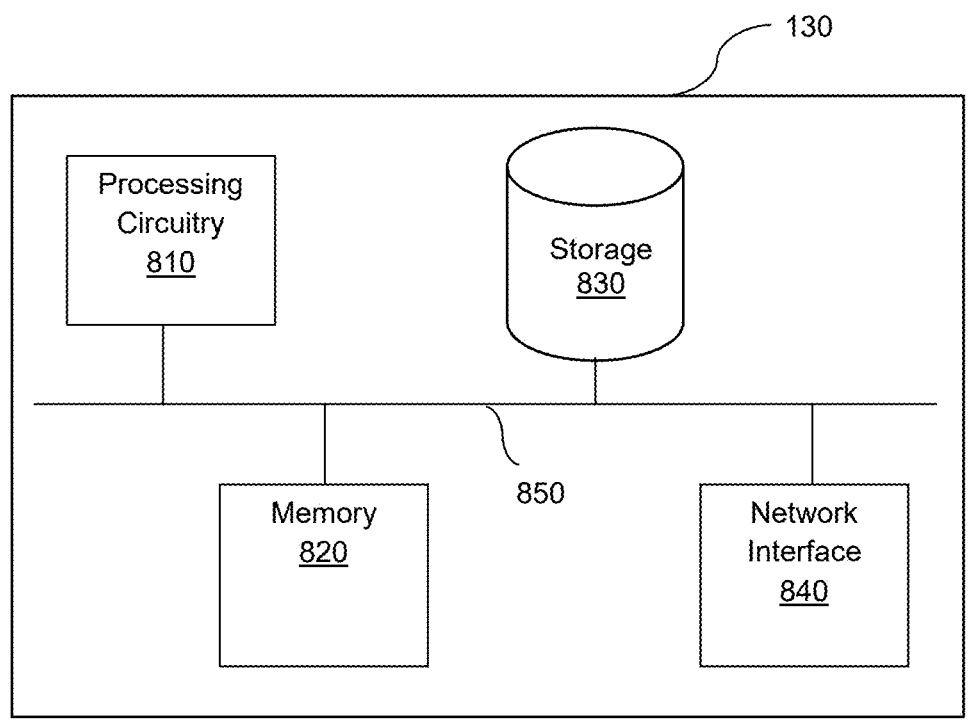
FIG. 8 is a schematic diagram of a GRN system according to an embodiment.

FIG. 8 is an example schematic diagram of a generative relational network (GRN) manager 130 according to an embodiment. The GRN manager 130 includes a processing circuitry 810 coupled to a memory 820, a storage 830, and a network interface 840. In an embodiment, the components of the GRN manager 130 may be communicatively connected via a bus 850.

The processing circuitry 810 may be realized as one or more hardware logic components and circuits. For example, and without limitation, illustrative types of hardware logic components that can be used include field programmable gate arrays (FPGAs), application-specific integrated circuits (ASICs), Application-specific standard products (ASSPs), system-on-a-chip systems (SOCs), graphics processing units (GPUs), tensor processing units (TPUs), general-purpose microprocessors, microcontrollers, digital signal processors (DSPs), and the like, or any other hardware logic components that can perform calculations or other manipulations of information.

The memory 820 may be volatile (e.g., random access memory, etc.), non-volatile (e.g., read only memory, flash memory, etc.), or a combination thereof.

In one configuration, software for implementing one or more embodiments disclosed herein may be stored in the storage 830. In another configuration, the memory 820 is configured to store such software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the processing circuitry 810, cause the processing circuitry 810 to perform the various processes described herein.

The storage 830 may be magnetic storage, optical storage, and the like, and may be realized, for example, as flash memory or other memory technology, compact disk-read only memory (CD-ROM), Digital Versatile Disks (DVDs), or any other medium which can be used to store the desired information.

The network interface 840 allows the GRN manager 130 to communicate with other systems, devices, components, applications, or other hardware or software components, for example as described herein.

It should be understood that the embodiments described herein are not limited to the specific architecture illustrated in FIG. 8, and other architectures may be equally used without departing from the scope of the disclosed embodiments.

Figure 9:
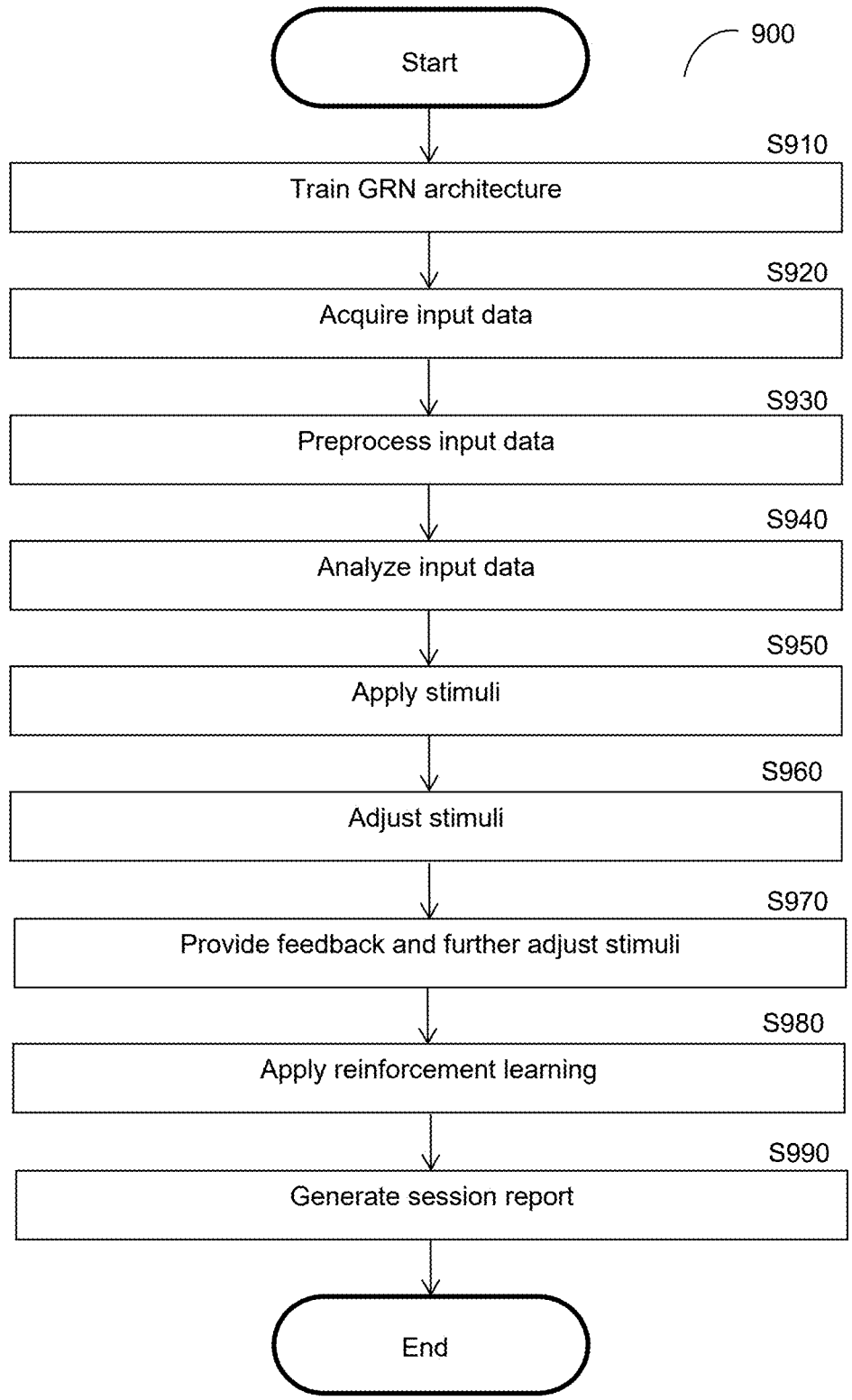
FIG. 9 is a flowchart illustrating a method for neurofeedback processing using a generative relational network according to an embodiment.

FIG. 9 is an example flowchart 900 illustrating a method for neurofeedback processing using a generative relational network (GRN) according to an embodiment. In an embodiment, the method is performed by the GRN manager 130, FIG. 1.

At S910, a GRN architecture is trained. In an embodiment, the GRN architecture is trained as discussed above, for example as discussed with respect to FIGS. 2 and 4.

At S920, input data is acquired. In an embodiment, S920 includes collecting or retrieving data such as, but not limited to, EEG signals and user responses to stimuli (e.g., audio stimuli).

At S930, the input data is preprocessed. In an embodiment, preprocessing the data includes extracting relevant features (i.e., features relevant to a given treatment). In a further embodiment, the preprocessing includes cleaning the input data. When the input data is or includes signals, the preprocessing may further include applying one or more signal processing techniques (e.g., filtering, artifact removal, both, etc.) in order to clean the signal data.

At S940, the extracted features are analyzed. In an embodiment, the extracted features are analyzed using reinforcement learning, supervised learning, or both. In a further embodiment, a state (e.g., a cognitive or emotional state of a patient) may be classified based on the analysis.

At S950, one or more stimuli are applied to a patient based on the analysis. In an embodiment, S950 includes selecting such stimuli based on the analysis. In an embodiment, the stimuli include electrical stimuli (e.g., electromagnetic stimuli). As a non-limiting example, such electrical stimuli may be delivered via a repetitive transcranial magnetic stimulation (rTMS) session in which an electromagnetic coil is placed against a scalp of the patient.

In some embodiments, the stimuli may further include media stimuli. Such media stimuli may accentuate effects of other stimuli, thereby improving results. The media stimuli may also be selected (e.g., by selecting specific portions of media to be used as stimuli) based on the analysis of the extracted features. As a non-limiting example, the stimuli may include audio inputs, and the specific audio inputs (e.g., particular songs or sets of songs as musical audio inputs) may be selected.

At S960, the stimuli are dynamically adjusted based on further input data. More specifically, the stimuli may be adjusted based on analysis of signals or other data captured as the stimuli are being applied. To this end, in a further embodiment, adjusting the stimuli includes adjusting stimulation parameters. As a non-limiting example, rTMS parameters such as, but not limited to, frequency, intensity, and location, may be adjusted in order to modify the stimulation. The stimuli may be dynamically adjusted by modifying or otherwise adjusting the stimuli in real-time as the stimuli are being applied in response to new inputs captured during the application. When the stimuli include media stimuli, adjusting the stimuli may include selecting new media for projection to the patient.

In an embodiment, the stimuli are dynamically adjusted based on one or more target outcomes defined with respect to input data being collected. Such target outcomes may be desired therapeutic outcomes or other outcomes to be achieved such that the stimulation may be modified until such target outcomes are achieved. As a non-limiting example for adjusting media stimuli, a music playlist may be customized in order to promote a target state as measured based on neurofeedback data.

At S970, feedback is provided to the patient and utilized to further adjust the stimuli. The feedback may be provided, for example but not limited to, via one or more user interfaces (e.g., a visual, auditory, or haptic interface). When the stimulation is or includes neurostimulation (e.g., electrical stimulation applied to neurons of a brain of the patient), neurofeedback parameters may be adjusted dynamically and utilized to deliver the feedback.

Based on the feedback, the patient's responses may change and be captured as new inputs. Such new inputs may be utilized in order to further adjust the stimuli, provide additional feedback, both, and the like. To this end, feedback and stimuli adjustment may be performed continuously (e.g., during a session), iteratively (e.g., over a series of sessions), or both, over time.

At S980, reinforcement learning is applied based on the inputs captured in response to the feedback in order to learn responses of the patient to different feedback over time. In an embodiment, the reinforcement learning is conducted such that successful sessions where a target state is achieved are rewarded, and ineffective sessions in which a target state is not achieved are penalized. Such reinforcement learning would therefore train a model in order to make decisions which are likely to achieve a target state and to avoid situations in which a target state is not achieved.

In an embodiment, S980 includes training a machine learning model using reinforcement learning based on actions defined with respect to the stimulation parameters (e.g., locations of electrical stimulation, intensity, times, frequencies, musical or other media parameters for media stimulation, etc.). As noted above, such reinforcement learning may be performed such that stimulation parameters or groups of stimulation parameters which achieve a target state or otherwise bring a state of the patient closer to the target state are rewarded, while stimulation parameters or groups of stimulation parameters which achieve a target state or otherwise cause a state of the patient to further deviate from the target state are punished. To this end, the reinforcement learning may be performed using a set of reinforcement learning parameters which define a reward function with respect to the target state, thereby causing the reinforcement learning to train the machine learning model in order to maximize a cumulative reward by learning which actions are likely to advance toward the target state.

At S990, one or more sessions involving stimulation as discussed above are analyzed in order to generate one or more reports. Such reports may indicate results of the sessions such as, but not limited to, session effectiveness (e.g., ability to achieve a target state in a given session, for example for a certain amount of time or for an amount of time that is greater than that of a previous session).

In some embodiments, the process described with respect to FIG. 9 may be utilized to train a multi-modal adaptive feedback system in order to analyze potential causal mechanisms for neuropsychiatric illnesses such as, but not limited to, Alzheimer's disease. In a non-limiting example implementation, the GRN architecture may be utilized to target microglia for analysis by collecting data related to different bands (e.g., alpha, beta, delta, and theta bands) in order to identify potential hidden relationships between Apolipoprotein E4 (APOE4) and theta bands, which in turn might unearth a potential mechanism related to APOE4 and microglia activation which may be linked to Alzheimer's disease or other neuroprocessing disorders. Such a mechanism may take the form of a previously unidentified neuropeptide, which may be referred to as "Neuropeptide X" or "NX" for reference.

In such an example, NX is a hypothetical neuropeptide that plays a role in neuroplasticity, which in turn may affect the onset or progression of Alzheimer's disease. In this example, areas for potential locations of NX may be represented via inputs to the self-organizing map (SOM, e.g., the SOM 220, FIG. 2). Such inputs may include, but are not limited to, band information (e.g., data related to alpha, beta, delta, and theta bands), data indicative of oxytocin levels (e.g., bloodwork or saliva analysis results), both, and the like. These inputs (or features extracted from these inputs) may be utilized by the SOM in order to organize and represent potential areas as nodes and edges. The map derived from the SOM may be input to the nodes of the GRN (e.g., the nodes 230 through 250, FIG. 2) in order to train the GRN architecture to unearth potential hidden relationships and mechanisms of internal components related to microglia activation.

Once the GRN architecture has been trained, the GRN architecture may be applied to data from a patient in order to, for example, target stimulation (e.g., targeting certain neurons in the prefrontal cortex) as part of a treatment of the patient. To this end, data such as electroencephalogram (EEG) signals from the patient are collected during a neurofeedback session.

Once the GRN architecture has been trained, the GRN architecture may be applied to data from a patient collected during a neurofeedback session in order to target stimulation (e.g., targeting certain neurons in the prefrontal cortex) as part of a treatment of the patient. To this end, electroencephalogram (EEG) signals from the patient are collected during a neurofeedback session. User responses (e.g., emotional state, cognitive load, and relaxation level) are tracked via behavioral feedback, additional biological or psychophysiological markers, or both. Historical data (e.g., previous EEG patterns, responses to repetitive transcranial magnetic stimulation [rTMS]), scores based on responses to audio prompts, etc.) may be utilized to personalize the session to the patient.

Signal processing techniques such as filtering and artifact removal may be applied in order to clean the EEG data. Relevant features are extracted from the EEG data. Such relevant features may include, but are not limited to, power spectral density, band power (e.g., band power in alpha, beta, theta, and delta bands), both, and the like.

Reinforcement learning, supervised learning, or both, may be utilized to analyze the features extracted from the EEG data and to classify the patient's current cognitive or emotional state in a real-time neurofeedback analysis. The classification of the patient's cognitive or emotional state may be utilized to deliver a customized set of audio inputs (e.g., customized rTMS, a customized music playlist using auditory beat stimulation, both, etc.).

Based on the classified state of the patient, rTMS may be applied. The rTMS parameters (e.g., frequency, intensity, location, coil type, etc.) are adjusted based on real-time EEG data analysis and desired therapeutic outcomes. This adjustment is relevant to targeting certain brain regions associated with certain therapeutic outcomes (e.g., dorsolateral prefrontal cortex for depression). A music playlist for the patient may be further customized in real-time, for example by selecting appropriate music tracks or auditory beat stimulation (ABS) parameters based on real-time neurofeedback data for the patient in order to promote a desired state.

Feedback is provided to the patient and utilized to further adjust the stimuli. The feedback may be provided, for example but not limited to, via one or more user interfaces (e.g., a visual, auditory, or haptic interface). Neurofeedback parameters such as, but not limited to, rTMS stimulation settings and music ABS selections, may be adjusted dynamically in order to optimize engagement and progress. The feedback may include real-time graphs, sound modulations, or visualizations that reflect brainwave activity. This feedback may therefore guide the user toward achieving the desired state.

Reinforcement learning is applied based on the inputs captured in response to the feedback in order to learn responses of the patient to different feedback over time. In an embodiment, the reinforcement learning is conducted such that successful sessions where a target state (e.g., reduced anxiety, improved focus, etc.) is achieved are rewarded, and ineffective sessions in which a target state is not achieved are penalized. Such reinforcement learning would therefore train a model in order to make decisions which are likely to achieve a target state and to avoid situations in which a target state is not achieved. User inputs and clinical assessments may be incorporated periodically in order to fine-tune and validate the algorithm used for reinforcement learning as well as any models trained using reinforcement learning.

Based on results of the sessions involving stimulation, reports may be prepared for clinicians or practitioners to review session effectiveness and make manual adjustments as necessary. Such reports may highlight trends in EEG, responses to rTMS, and musical preferences.

In this regard, it is noted that microglia are the resident immune cells in the central nervous system and play a role in maintaining brain homeostasis, immune defense, and neuroinflammation modulation. Dysfunction in microglial activity is linked to various neurological and psychiatric disorders, including Alzheimer's disease, Parkinson's disease, depression, and schizophrenia. It is also noted that neurofeedback techniques such as quantitative electroencephalography (QEEG), electroencephalography (EEG), and repetitive transcranial magnetic stimulation (rTMS) can potentially improve microglial function by modulating neural circuits, reducing neuroinflammation, and enhancing neuroplasticity.

It is further noted that microglia are dynamic cells that constantly surveil the brain environment, respond to injury or infection, clear debris, and regulate synaptic pruning and neurogenesis. The dysregulated microglial function is associated with excessive inflammation, impaired synaptic connectivity, and neuronal death, contributing to cognitive decline and neurodegenerative diseases. Modulating microglial activity toward a neuroprotective phenotype may therefore provide beneficial effects in neurological therapeutics. Accordingly, it has been identified that using a GRN architecture as described herein in order to identify potential interactions affected by microglial activation may be utilized to more accurately and more granularly target certain regions of the brain for stimulation, which in turn may be utilized to better treat patients having or expected to have certain neuropsychiatric illnesses (e.g., by targeting certain regions of the brain for electromagnetic stimulation).

It is also noted that EEG and QEEG are non-invasive techniques for measuring electrical activity in the brain. QEEG provides a quantitative analysis which may be used to identify abnormal brainwave patterns associated with neuroinflammation and microglial dysfunction. It is further noted that certain EEG patterns correlate to certain neuroinflammatory states. For example, increased delta wave activity may be associated with neurodegenerative diseases where microglial activation is implicated. QEEG may therefore be utilized to help identify brain regions with abnormal electrical activity, which in turn may correspond to areas with microglial overactivation or dysfunction. This information can be used to target certain brain regions with rTMC in order to modulate microglial activity.

Moreover, EEG-based neurofeedback may be utilized to help patients train their brain activity by receiving real-time feedback on brainwave patterns, which may allow patients to indirectly influence microglial activation. By targeting certain EEG patterns associated with neuroinflammation, neurofeedback may be used to help recalibrate the brain's neuroimmune environment, thereby reducing chronic inflammation and promoting synaptic health.

Further, it is noted that rTMS is a non-invasive neuromodulation technique which uses magnetic fields to stimulate neuron activity in specific brain regions. It is also noted that rTMS may influence neuroimmune responses and play a role in modulating microglial activity. To this end, rTMS can suppress pro-inflammatory cytokine production (e.g., TNF-alpha, IL-1B) and enhance anti-inflammatory cytokines (e.g., IL-10), thereby creating a more balanced neuroimmune environment conducive to neuroprotection. Accordingly, it has been identified that, by reducing proinflammatory signals in the central nervous system (CNS), rTMS may be utilized to promote a shift in microglial phenotype from an M1 (pro-inflammatory) state to an M2 (anti-inflammatory) state, thereby supporting synaptic repair, neurogenesis, and overall brain health.

In relation to microglia, it is noted that certain brain regions (e.g., the prefrontal cortex, hippocampus, and motor cortex) are associated with cognitive function, mood regulation, and neuroimmune responses. It is further noted that ITMS applied to the prefrontal cortex can influence microglial activation indirectly by modulating glutamatergic and dopaminergic neurotransmission, which are linked to neuroinflammatory processes. Accordingly, it has been identified that targeting these regions with certain rTMS parameters may enhance microglial response and promote neuroprotection in conditions such as Alzheimer's disease, depression, and traumatic brain injury.

Combing the above findings, it has been identified that combining rTMC with EEG and/or QEEG in a closed-loop system may allow for real-time modulation of brain activity in order to optimize microglial function. By continuously monitoring EEG signals, such a system could dynamically adjust rTMC parameters in order to target abnormal brain activity patterns associated with neuroinflammation. Accordingly, in an embodiment, the system realized using the process of FIG. 9 may adjust rTMC parameters in this way in order to enhance cognitive function, reduce neuroinflammation, both, and the like. As noted above, this may be used to treat patients experiencing or expected to experience in the future certain neuropsychiatric disorders by normalizing microglial activity and reducing neurodegenerative processes. Moreover, such embodiments may be used to improve mood regulation by modulating microglial function. Additionally, such embodiments may be used to assess regions of the brain affected by traumatic brain injury (TBI) and applying targeted rTMS in order to promote microglial-mediated neuroprotection and recovery in TBI patients.

It is important to note that the embodiments disclosed herein are only examples of the many advantageous uses of the innovative teachings herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

The various embodiments disclosed herein can be implemented as hardware, firmware, software, or any combination thereof. Moreover, the software may be implemented as an application program tangibly embodied on a program storage unit or computer readable medium consisting of parts, or of certain devices and/or a combination of devices. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such a computer or processor is explicitly shown. In addition, various other peripheral units may be connected to the computer platform such as an additional data storage unit and a printing unit. Furthermore, a non-transitory computer readable medium is any computer readable medium except for a transitory propagating signal.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

It should be understood that any reference to an element herein using a designation such as "first," "second," and so forth does not generally limit the quantity or order of those elements. Rather, these designations are generally used herein as a convenient method of distinguishing between two or more elements or instances of an element. Thus, a reference to first and second elements does not mean that only two elements may be employed there or that the first element must precede the second element in some manner. Also, unless stated otherwise, a set of elements comprises one or more elements.

As used herein, the phrase "at least one of" followed by a listing of items means that any of the listed items can be utilized individually, or any combination of two or more of the listed items can be utilized. For example, if a system is described as including "at least one of A, B, and C," the system can include A alone; B alone; C alone; 2A; 2B; 2C; 3A; A and B in combination; B and C in combination; A and C in combination; A, B, and C in combination; 2A and C in combination; A, 3B, and 2C in combination; and the like.

What is claimed is:

1. A method for identifying relationships using relational networks, comprising:
    applying a generative relational network (GRN) in order to create a model of relationships between entities among a plurality of entities, wherein the GRN includes a plurality of sets of nodes, each set of nodes including a respective set of machine learning models, wherein the plurality of sets of nodes include a set of dominance factor nodes and a set of evolution of internal component nodes, wherein the set of dominance factor nodes defines a dominance factor based on change intensity and change frequency, wherein the set of evolution of internal component nodes defines evolution with respect to changes determined based on values of the dominance factor over time, wherein the plurality of entities is a plurality of neurotransmitters;
    simulating a plurality of relationships among the plurality of entities using the model in order to produce simulation results, wherein the plurality of relationships correspond to a plurality of respective locations;
    eliminating at least a portion of the plurality of relationships for a target interaction based on the simulation results in order to determine a set of remaining relationships for the target interaction;

testing relationships among the set of remaining relationships with respect to the target interaction; and identifying the target interaction based on the testing of the relationships among the set of remaining relationships;

identifying a first neurotransmitter of the plurality of neurotransmitters, wherein the first neurotransmitter is identified as being a neurotransmitter of the target interaction based on the locations of the relationships among the set of remaining relationships; and treating a patient by stimulating the patient with respect to the first neurotransmitter.

2. The method of claim 1, wherein the GRN is trained based on a visualization created using a self-organizing map.

3. The method of claim 1, wherein simulating the plurality of relationships among the plurality of entities further comprises:

simulating a plurality of activities.

4. The method of claim 1, wherein eliminating the at least a portion of the plurality of relationships further comprises:

analyzing the simulation results in order to determine whether an expected reaction is demonstrated in the simulation results for each of the simulated plurality of relationships and eliminating each relationship for which the simulation results lack the expected reaction.

5. The method of claim 1, further comprising:

identifying a first entity among the plurality of entities, wherein the first entity is involved in the target interaction.

6. The method of claim 1, wherein the first neurotransmitter is identified with respect to one of the locations of the relationships among the set of remaining relationships, wherein the patient is stimulated at least at the location of the target neurotransmitter.

7. The method of claim 1, wherein stimulating the patient further comprises:

delivering a repetitive transcranial magnetic stimulation.

8. The method of claim 7, wherein stimulating the patient further comprises:

providing at least one media stimulus to the patient.

9. The method of claim 1, further comprising:

adjusting at least one stimulation parameter based on inputs captured while the patient is being stimulated, wherein the at least one stimulation parameter is adjusted based on a target outcome defined with respect to the inputs captured while the patient is being stimulated.

10. A non-transitory computer readable medium having stored thereon instructions for causing a processing circuitry to execute a process, the process comprising:

applying a generative relational network (GRN) in order to create a model of relationships between entities among a plurality of entities, wherein the GRN includes a plurality of sets of nodes, each set of nodes including a respective set of machine learning models, wherein the plurality of sets of nodes include a set of dominance factor nodes and a set of evolution of internal component nodes, wherein the set of dominance factor nodes defines a dominance factor based on change intensity and change frequency, wherein the set of evolution of internal component nodes defines evolution with respect to changes determined based on values of the dominance factor over time, wherein the plurality of entities is a plurality of neurotransmitters;

simulating a plurality of relationships among the plurality of entities using the model in order to produce simulation results, wherein the plurality of relationships correspond to a plurality of respective locations;

eliminating at least a portion of the plurality of relationships for a target interaction based on the simulation results in order to determine a set of remaining relationships for the target interaction;

testing relationships among the set of remaining relationships with respect to the target interaction;

identifying the target interaction based on the testing of the relationships among the set of remaining relationships;

identifying a first neurotransmitter of the plurality of neurotransmitters, wherein the first neurotransmitter is identified as being a neurotransmitter of the target interaction based on the locations of the relationships among the set of remaining relationships; and treating a patient by stimulating the patient with respect to the first neurotransmitter.

11. A system for identifying relationships using relational networks, comprising:

a processing circuitry; and a memory, the memory containing instructions that, when executed by the processing circuitry, configure the system to:

apply a generative relational network (GRN) in order to create a model of relationships between entities among a plurality of entities, wherein the GRN includes a plurality of sets of nodes, each set of nodes including a respective set of machine learning models, wherein the plurality of sets of nodes include a set of dominance factor nodes and a set of evolution of internal component nodes, wherein the set of dominance factor nodes defines a dominance factor based on change intensity and change frequency, wherein the set of evolution of internal component nodes defines evolution with respect to changes determined based on values of the dominance factor over time, wherein the plurality of entities is a plurality of neurotransmitters;

simulate a plurality of relationships among the plurality of entities using the model in order to produce simulation results, wherein the plurality of relationships correspond to a plurality of respective locations;

eliminate at least a portion of the plurality of relationships for a target interaction based on the simulation results in order to determine a set of remaining relationships for the target interaction;

test relationships among the set of remaining relationships with respect to the target interaction; and identify the target interaction based on the testing of the relationships among the set of remaining relationships;

identify a first neurotransmitter of the plurality of neurotransmitters, wherein the first neurotransmitter is identified as being a neurotransmitter of the target interaction based on the locations of the relationships among the set of remaining relationships; and treat a patient by stimulating the patient with respect to the first neurotransmitter.

12. The system of claim 11, wherein the GRN is trained based on a visualization created using a self-organizing map.

13. The system of claim 11, wherein the system is further configured to:

simulate a plurality of activities.

14. The system of claim 11, wherein the system is further configured to:

analyze the simulation results in order to determine whether an expected reaction is demonstrated in the simulation results for each of the simulated plurality of relationships and eliminating each relationship for which the simulation results lack the expected reaction.

15. The system of claim 11, wherein the system is further configured to:
   identify a first entity among the plurality of entities, wherein the first entity is involved in the target interaction.

16. The system of claim 11, wherein the first neurotransmitter is identified with respect to one of the locations of the relationships among the set of remaining relationships, wherein the patient is stimulated at least at the location of the target neurotransmitter.

17. The system of claim 11, wherein the system is further configured to:
   deliver a repetitive transcranial magnetic stimulation.

18. The system of claim 17, wherein the system is further configured to:
   provide at least one media stimulus to the patient.

19. The system of claim 11, wherein the system is further configured to:
   adjust at least one stimulation parameter based on inputs captured while the patient is being stimulated, wherein the at least one stimulation parameter is adjusted based on a target outcome defined with respect to the inputs captured while the patient is being stimulated.

* * * * *